US008242085B2

(12) United States Patent
Babu et al.

(10) Patent No.: US 8,242,085 B2
(45) Date of Patent: Aug. 14, 2012

(54) TETRAHYDROFURO [3,4-D] DIOXOLANE COMPOUNDS FOR USE IN THE TREATMENT OF VIRAL INFECTIONS AND CANCER

(75) Inventors: Yarlagadda S. Babu, Birmingham, AL (US); Pooran Chand, Birmingham, AL (US)

(73) Assignee: BioCryst Pharmaceuticals, Inc., Durham, NC (US)

( * ) Notice: Subject to any disclaimer, the term of this patent is extended or adjusted under 35 U.S.C. 154(b) by 192 days.

(21) Appl. No.: 12/599,656

(22) PCT Filed: May 8, 2008

(86) PCT No.: PCT/US2008/063037
§ 371 (c)(1),
(2), (4) Date: Nov. 10, 2009

(87) PCT Pub. No.: WO2008/141079
PCT Pub. Date: Nov. 20, 2008

(65) Prior Publication Data
US 2011/0002886 A1  Jan. 6, 2011

Related U.S. Application Data

(60) Provisional application No. 60/917,210, filed on May 10, 2007, provisional application No. 60/940,125, filed on May 25, 2007.

(51) Int. Cl.
*A01N 43/04* (2006.01)
*A61K 31/70* (2006.01)
*C07H 19/00* (2006.01)

(52) U.S. Cl. ............... 514/23; 514/260.1; 536/29.2

(58) Field of Classification Search .......... None
See application file for complete search history.

(56) References Cited

U.S. PATENT DOCUMENTS

| 7,429,571 | B2 | 9/2008 | Chand et al. |
| 7,514,410 | B2 | 4/2009 | Babu et al. |
| 7,994,139 | B2 | 8/2011 | Babu et al. |
| 2008/0300200 | A1 | 12/2008 | Babu et al. |
| 2009/0247750 | A1 | 10/2009 | Kotian et al. |
| 2010/0015094 | A1 | 1/2010 | Babu et al. |
| 2010/0093991 | A1 | 4/2010 | Chand et al. |
| 2010/0143300 | A1 | 6/2010 | Babu et al. |
| 2011/0144321 | A1 | 6/2011 | Chand et al. |

FOREIGN PATENT DOCUMENTS

| WO | WO 2005/123087 A2 | 12/2005 |
| WO | WO 2006/050161 A2 | 5/2006 |
| WO | WO 2006/104945 A2 | 10/2006 |
| WO | WO 2007/002191 A2 | 1/2007 |
| WO | WO 2007/021610 A2 | 2/2007 |
| WO | WO 2008/089105 A2 | 7/2008 |
| WO | WO 2008/141079 A1 | 11/2008 |
| WO | WO 2009/111653 A2 | 9/2009 |
| WO | WO 2010/011748 A2 | 1/2010 |

OTHER PUBLICATIONS

Butora et al., Bioorganic and Medicinal Chemistry, vol. 15 (15), Jun. 2007, 5219-5229.*
Blight et al., "Efficient Initiation of HCV RNA Replication in Cell Culture", *Science* vol. 290, pp. 1972-1974, 2000.
Bruenn, J.A. "Relationships among the positive strand and double-strand RNA viruses as viewed through their RNA-dependent RNA polymerases", *Nucleic Acids Research*, vol. 19, No. 2, pp. 217-226, 1991.
Davis, "Current Therapy for Chronic Hepatitis C", *Gastroenterology* vol. 118, pp. S104-S114, 2000.
DeLuca et al., "Parenteral Drug-Delivery Systems", *Pharmaceutics and Pharmacy Practice*, pp. 238-250, 1982.
Korba et al., "Use of a standardized cell culture assay to assess activities of nucleoside analogs against hepatitis B virus replication", *Antivir. Res*, vol. 19, No. 1, pp. 55-70, 1992.
Okuse et al., "Enhancement of antiviral activity against hepatitis C virus in vitro by interferon combination therapy", *Antiviral Res.* vol. 65, pp. 23-34, 2005.
Patent Cooperation Treaty International Search Report and Written Opinion of the International Searching Authority, PCT/US2008/063037, 8 pages, Aug. 6, 2008.
Trissel, *ASHP Handbook on Injectable Drugs*, 4$^{th\ ed.}$, pp. 622-630, 1986.

* cited by examiner

*Primary Examiner* — Traviss C McIntosh, III
(74) *Attorney, Agent, or Firm* — Dana M. Gordon; Foley Hoag LLP

(57) ABSTRACT

The invention provides compounds of formula (I), as described herein, or pharmaceutically acceptable salts thereof, as well as pharmaceutical compositions comprising the compounds, and synthetic methods and intermediates that are useful for preparing the compounds. The compounds of formula (I) are useful as anti-viral agents and/or as anti-cancer agents.

46 Claims, No Drawings

TETRAHYDROFURO [3,4-D] DIOXOLANE COMPOUNDS FOR USE IN THE TREATMENT OF VIRAL INFECTIONS AND CANCER

RELATED APPLICATIONS

This patent document claims the benefit of priority of U.S. application Ser. No. 60/917,210, filed May 10, 2007, and of U.S. application Ser. No. 60/940,125, filed May 25, 2007, which applications are herein incorporated by reference.

BACKGROUND OF THE INVENTION

Viral diseases are a major cause of death and economic loss in the world.

The Flaviviridae family of viruses consists of three genera: the flaviviruses (including dengue, West Nile, and yellow fever viruses), hepacivirus (HCV), and the Pestiviruses (including bovine viral diarrhea virus, BVDV). The disease states and conditions caused by members of this family include yellow fever, dengue, Japanese encephalitis, St. Louis encephalitis, Hepatitis B and C, West Nile disease, and AIDS. Currently, human immunodeficiency virus (HIV), hepatitis B virus (HBV) and hepatitis C virus (HCV) infections are responsible for the largest number of viral related deaths worldwide. Although there are some drugs useful for treating HIV, there are only a few drugs useful for treating HBV, and no drugs that are broadly useful for treating HCV.

Ribavirin (1-β-D-ribofuranosyl-1-1,2,4-triazole-3-carboxamide) is a synthetic, non-interferon-inducing, broad spectrum antiviral nucleoside. Ribavirin is structurally similar to guanosine, and has in vitro activity against several DNA and RNA viruses including Flaviviridae (Davis. Gastroenterology 118:S104-S114, 2000). Ribavirin reduces serum amino transferase levels to normal in 40% of patients, but it does not lower serum levels of HCV-RNA (Davis. Gastroenterology 118:S104-S114, 2000). Thus, ribavirin alone is not effective in reducing viral RNA levels. Additionally, ribavirin has significant toxicity and is known to induce anemia.

Interferons (IFNs) are compounds which have been commercially available for the treatment of chronic hepatitis for nearly a decade. IFNs are glycoproteins produced by immune cells in response to viral infection. IFNs inhibit viral replication of many viruses, including HCV. When used as the sole treatment for hepatitis C infection, IFN suppresses serum HCV-RNA to undetectable levels. Additionally, IFN normalizes serum amino transferase levels. Unfortunately, the effects of IFN are temporary and a sustained response occurs in only 8%-9% of patients chronically infected with HCV (Davis. Gastroenterology 118:S104-S114, 2000).

HCV is a positive stranded ss RNA virus with a well characterized RNA-dependent RNA polymerase (RdRp) and a well characterized disease progression. HCV has infected an estimated 170 million people worldwide, leading to a major health crisis as a result of the disease. Indeed, during the next few years the number of deaths from HCV-related liver disease and hepatocellular carcinoma may overtake those caused by AIDS. Egypt is the hardest hit country in the world, with 23% of the population estimated to be carrying the virus; whereas, in the USA the prevalence of chronic infections has recently been determined to be around 1.87% (2.7 million persons). HCV infections become chronic in about 50% of cases. Of these, about 20% develop liver cirrhosis that can lead to liver failure, including hepatocellular carcinoma.

The NS5B region of HCV encodes a 65 KDa RdRp thought to be responsible for viral genome replication. RdRps function as the catalytic subunit of the viral replicase required for the replication of all positive-strand viruses. The NS5B protein has been well characterized, shown to possess the conserved GDD motif of RdRps and in vitro assay systems have been reported. Cellular localization studies revealed that NS5B is membrane-associated in the endoplasmic reticulum like NS5A, suggesting that those two proteins may remain associated with one another after proteolytic processing. Additional evidence suggests that NS3, NS4A and NS5B interact with each other to form a complex that functions as part of the replication machinery of HCV.

The X-ray crystal structure of NS5B apoenzyme has been determined and three very recent publications describe the unusual shape of the molecule. This unique shape for a polymerase, resembling a flat sphere, is attributed to extensive interactions between the fingers and thumb subdomains in such a way that the active site is completely encircled, forming a cavity 15 Å across and 20 Å deep. Modeling studies showed that the NS5B apoenzyme can accommodate the template-primer without large movement of the subdomains, suggesting that the structure is preserved during the polymerization reaction. The RdRp polypeptides from various members of the Flaviviridae family and other viral families have been shown to be conserved (J. A. Bruenn, Nucleic Acids Research, Vol. 19, No. 2 p. 217, 1991).

Currently, there are no safe and effective therapeutic agents on the market that target HCV polymerase. There is currently a need for therapeutic agents and therapeutic methods that are useful for treating viral infections, such as HCV, HIV, and HBV.

In addition, there is also a current need for therapeutic agents and therapeutic methods that are useful for treating cancer. Even though significant advances have occurred in the treatment of cancer, it still remains a major health concern. It has been reported that cancer is the cause of death of up to one of every four Americans. Notwithstanding the advances in treatments for cancer and other diseases, there is still a need for novel drugs that are effective to treat cancer.

SUMMARY OF CERTAIN EMBODIMENTS OF THE INVENTION

The present invention provides compounds that are inhibitors of viral RNA and DNA polymerases (e.g. polymerases from hepatitis B, hepatitis C, human immunodeficiency virus, Polio, Coxsackie A and B, Rhino, Echo, small pox, Ebola, and West Nile virus) and that are useful for treating HCV, as well as other viral infections (e.g. flaviviral infections), and cancer.

Accordingly, the invention provides novel compounds of formula I as described herebelow, or a pharmaceutically acceptable salt thereof.

The invention also provides a pharmaceutical composition comprising a compound of formula I, or a pharmaceutically acceptable salt thereof, and a pharmaceutically acceptable carrier. The composition can optionally comprise one or more additional anti-viral and/or anti-cancer agents.

In certain embodiments, the one or more anti-viral agents are selected from ribavirin, levovirin, viramidine, thymosin alpha-1, an inhibitor of serine proteases, an inhibitor of inosine monophosphatedehydrognease, interferon-α, and pegylated interferon-α (peginterferon-α).

In certain embodiments, the one or more anti-cancer agents are selected from alkylating agents, antimetabolites, natural products, and hormonal agents.

In certain embodiments, the composition further comprises one or more additional HCV polymerase inhibitors.

In certain embodiments, the composition further comprises one or more protease inhibitors.

In certain embodiments, the composition further comprises ribavirin.

In certain embodiments, the composition further comprises interferon-α or pegylated interferon-α (peginterferon-α).

The invention also provides a method for treating a viral infection in an animal comprising administering to the animal an effective amount of a compound of formula I, or a pharmaceutically acceptable salt thereof.

The invention also provides a method for inhibiting a viral RNA or DNA polymerase comprising contacting the polymerase (in vitro or in vivo) with an effective inhibitory amount of a compound of formula I, or a pharmaceutically acceptable salt thereof.

The invention also provides a method for treating cancer in an animal comprising administering to the animal an effective amount of a compound of formula I, or a pharmaceutically acceptable salt thereof.

The invention also provides a compound of formula I, or a pharmaceutically acceptable salt thereof, for use in medical therapy (e.g. for use in treating a viral infection or for use in treating cancer).

The invention also provides the use of a compound of formula I, or a pharmaceutically acceptable salt thereof, to prepare a medicament useful for treating a viral infection in an animal (e.g. a human).

The invention also provides the use of a compound of formula I, or a pharmaceutically acceptable salt thereof, to prepare a medicament useful for treating cancer in an animal (e.g. a human).

The invention also provides a compound of formula I, or a pharmaceutically acceptable salt thereof, for use in therapy.

The invention also provides the use of a compound of formula I, or a pharmaceutically acceptable salt thereof, for treating a viral infection in an animal (e.g. a human).

The invention also provides the use of a compound of formula I, or a pharmaceutically acceptable salt thereof, for treating cancer in an animal (e.g. a human).

The invention also provides a method for treating a viral infection in an animal comprising administering to the animal a pharmaceutically effective amount of a compound of the invention, or a composition of the invention.

In certain embodiments, the viral infection is selected from the group consisting of: hepatitis B, hepatitis C, human immunodeficiency virus, Polio, Coxsackie A and B, Rhino, Echo, small pox, Ebola, and West Nile virus.

In certain embodiments, the viral infection is HCV.

In certain embodiments, the method further comprises administering to the animal one or more additional HCV polymerase inhibitors.

In certain embodiments, the method further comprises administering to the animal one or more protease inhibitors.

In certain embodiments, the method further comprises administering ribavirin to the animal.

In certain embodiments, the method further comprises administering interferon-α or pegylated interferon-α (peginterferon-α) to the animal.

The invention also provides a method for treating cancer in an animal comprising administering to the animal a pharmaceutically effective amount of a compound of the invention, or a composition as of the invention.

In certain embodiments, one or more additional anti-cancer agents are administered.

In certain embodiments, the animal is a human.

In certain embodiments, the viral polymerase is an RdRp.

The invention also provides novel synthetic intermediates and synthetic methods that are disclosed herein as being useful for preparing compounds of formula I. Some compounds of formula I may be useful as synthetic intermediates for preparing other compounds of formula I.

DETAILED DESCRIPTION

Definitions

The term "pharmaceutically acceptable salt" as used herein refers to a compound of the present disclosure derived from pharmaceutically acceptable bases, inorganic or organic acids. Examples of suitable acids include, but are not limited to, hydrochloric, hydrobromic, sulfuric, nitric, perchloric, fumaric, maleic, phosphoric, glycollic, lactic, salicyclic, succinic, toluene-p-sulfonic, tartaric, acetic, citric, methanesulfonic, formic, benzoic, malonic, naphthalene-2-sulfonic, trifluoroacetic and benzenesulfonic acids. Salts derived from appropriate bases include, but are not limited to, alkali such as sodium and ammonia.

The terms "treat", "treating" and "treatment" as used herein include administering a compound prior to the onset of clinical symptoms of a disease state/condition so as to prevent any symptom, as well as administering a compound after the onset of clinical symptoms of a disease state/condition so as to reduce or eliminate any symptom, aspect or characteristic of the disease state/condition. Such treating need not be absolute to be useful.

The term "animal" as used herein refers to any animal, including mammals, such as, but not limited to, mice, rats, other rodents, rabbits, dogs, cats, swine, cattle, sheep, horses, and primates. In one specific embodiment of the invention the animal is a human.

The term "pharmaceutically effective amount", in reference to treating a disease state/condition, refers to an amount of a compound either alone or as contained in a pharmaceutical composition that is capable of having any detectable, positive effect on any symptom, aspect, or characteristics of a disease state/condition when administered as a single dose or in multiple doses. Such effect need not be absolute to be beneficial.

The term "alkyl" as used herein refers to alkyl groups having from 1 to 6 carbon atoms. This term is exemplified by groups such as methyl, ethyl, n-propyl, iso-propyl, n-butyl, t-butyl, n-pentyl and the like. In a specific embodiment, the alkyl groups have from 1-4 carbon atoms and are referred to as lower alkyl.

The term "substituted alkyl" as used herein refers to an alkyl group having from 1 to 3 substituents, said substituents being selected from the group consisting of alkoxy, substituted alkoxy, acyl, substituted acyl, acylamino, acyloxy, oxyacyl, amino, substituted amino, aminoacyl, aryl, substituted aryl, aryloxy, substituted aryloxy, cyano, halogen, hydroxyl, nitro, $N_3$, carboxyl, carboxyl esters, thiol, thioalkyl, substituted thioalkyl, thioaryl, substituted thioaryl, thioheteroaryl; substituted thioheteroaryl, thiocycloalkyl, substituted thiocycloalkyl, thioheterocyclic, substituted thioheterocyclic, cycloalkyl, substituted cycloalkyl, heteroaryl, substituted heteroaryl, heterocyclic, and substituted heterocyclic.

The terms "alkenyl" or "alkene" as used herein refers to an alkenyl group having from 2 to 10 carbon atoms and having at least 1 site of alkenyl unsaturation. Such groups are exemplified by vinyl(ethen-1-yl), allyl, but-3-en-1-yl, and the like.

The term "substituted alkenyl" as used herein refers to alkenyl groups having from 1 to 3 substituents, said substituents being selected from those described above for a substituted alkyl.

The term "alkynyl" or "alkyne" as used herein refers to an alkynyl group having from 2-10 carbon atoms and having at least 1 site of alkynyl unsaturation. Such groups are exemplified by, but not limited to, ethyn-1-yl, propyn-1-yl, propyn-2-yl, 1-methylprop-2-yn-1-yl, butyn-1-yl, butyn-2-yl, butyn-3-yl, and the like.

The term "substituted alkynyl" as used herein refers to alkynyl groups having from 1 to 3 substituents, said substituents being selected from those described above for a substituted alkyl.

The term "alkoxy" refers to the group alkyl-O—.

The term "substituted alkoxy" as used herein refers to the group substituted alkyl-O—.

The term "acyl" as used herein refers to the groups alkyl-C(O)—, alkenyl-C(O)—, alkynyl-C(O)—, cycloalkyl-C(O)—, aryl-C(O)—, heteroaryl-C(O)—, and heterocyclic-C(O).

The term "substituted acyl" as used herein refers to the groups substituted alkyl-C(O)—, substituted alkenyl-C(O)—, substituted alkynyl-C(O)—, substituted cycloalkyl-C(O)—, substituted aryl-C(O)—, substituted heteroaryl-C(O), and substituted heterocyclic-C(O)—.

The term "acylamino" as used herein refers to the group-C(O)NZ$_1$Z$_2$ where each Z$_1$ and Z$_2$ are independently selected from the group consisting of hydrogen, alkyl, substituted alkyl, alkenyl, substituted alkenyl, alkynyl and substituted alkynyl, and the substituents described above in the definition of substituted alkyl.

The term "acyloxy" as used herein refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O—.

The term "oxyacyl" as used herein refers to the groups alkyl-OC(O)—, substituted alkyl-OC(O)—, alkenyl-OC(O)—, substituted alkenyl-OC(O)—, alkynyl-OC(O)—, substituted alkynyl-OC(O)—, aryl-OC(O)—, substituted aryl-OC(O)—, cycloalkyl-OC(O)—, substituted cycloalkyl-OC(O)—, heteroaryl-OC(O)—, substituted heteroaryl-OC(O)—, heterocyclic-OC(O)—, and substituted heterocyclic-OC(O)—.

The term "amino" as used herein refers to the group —NH$_2$.

The term "substituted amino" as used herein refers to the group-N Z$_1$Z$_2$ where Z$_1$ and Z$_2$ are as described above in the definition of acylamino, provided that Z$_1$ and Z$_2$ are both not hydrogen.

The term "aminoacyl" as used herein refers to the groups —NZ$_3$C(O)alkyl, —NZ$_3$C(O)substituted alkyl, —NZ$_3$C(O)cycloalkyl, —NZ$_3$C(O)substituted cycloalkyl, —NZ$_3$C(O)alkenyl, —NZ$_3$C(O)substituted alkenyl, —NZ$_3$C(O)alkynyl, —NZ$_3$C(O)substituted alkynyl, —NZ$_3$C(O)aryl, —NZ$_3$C(O)substituted aryl, —NZ$_3$C(O)heteroaryl, —NZ$_3$C(O)substituted heteroaryl, —NZ$_3$C(O)heterocyclic, and —NZ$_3$C(O)substituted heterocyclic, where Z$_3$ is hydrogen or alkyl.

The term "aryl" as used herein refers to a monovalent aromatic cyclic group of from 6 to 14 carbon atoms having a single ring (e.g., phenyl) or multiple condensed rings (e.g., naphthyl or anthryl) which condensed rings may or may not be aromatic. Exemplary aryls include, but are not limited to, phenyl and naphthyl.

The term "substituted aryl" as used herein refers to aryl groups which are substituted with from 1 to 3 substituents selected from alkyl, substituted alkyl, alkenyl, substituted alkenyl, alkynyl and substituted alkynyl, and those substituents described above in the definition of substituted alkyl.

The term "aryloxy" as used herein refers to the group aryl-O— that includes, by way of example but not limitation, phenoxy, naphthoxy, and the like.

The term "substituted aryloxy" as used herein refers to substituted aryl-O-groups.

The term "carboxyl" as used herein refers to —COOH or salts thereof.

The term "carboxyl esters" as used herein refers to the groups-C(O)O-alkyl, —C(O)O-substituted alkyl, —C(O)O-aryl, and-C(O)O-substituted aryl.

The term "cycloalkyl" as used herein refers to a saturated or unsaturated cyclic hydrocarbon ring systems, such as those containing 1 to 3 rings and 3 to 7 carbons per ring. Exemplary groups include but are not limited to cyclopropyl, cyclobutyl, cyclopentyl, cyclohexyl, cycloheptyl, and adamantyl.

The term "substituted cycloalkyl" as used herein refers to a cycloalkyl having from 1 to 5 substituents selected from the group consisting of oxo (=O), thioxo (=S), alkyl, substituted alkyl, and those substituents described in the definition of substituted alkyl.

The term "cycloalkoxy" as used herein refers to —O-cycloalkyl groups.

The term "substituted cycloalkoxy" as used herein refers to-O-substituted cycloalkyl groups.

The term "formyl" as used herein refers to HC(O)—.

The term "halogen" as used herein refers to fluoro, chloro, bromo and iodo.

The term "heteroaryl" as used herein refers to an aromatic group of from 1 to 10 carbon atoms and 1 to 4 heteroatoms selected from the group consisting of oxygen, nitrogen, sulfur in the ring. The sulfur and nitrogen heteroatoms atoms may also be present in their oxidized forms. Such heteroaryl groups can have a single ring (e.g., pyridyl or furyl) or multiple condensed rings (e.g., indolizinyl or benzothienyl) wherein the condensed rings may or may not be aromatic and/or contain a heteroatom. Exemplary heteroaryl groups include, but are not limited to, pyridyl, pyrrolyl, thienyl, indolyl, thiophenyl, and furyl.

The term "substituted heteroaryl" as used herein refers to heteroaryl groups that are substituted with from 1 to 3 substituents selected from the same group of substituents defined for substituted aryl.

The term "heteroaryloxy" as used herein refers to the group —O-heteroaryl.

The term "substituted heteroaryloxy" as used herein refers to the group —O-substituted heteroaryl.

The term "heterocycle" or "heterocyclic" or "heterocycloalkyl" refers to a saturated or unsaturated group (but not heteroaryl) having a single ring or multiple condensed rings, from 1 to 10 carbon atoms and from 1 to 4 hetero atoms selected from the group consisting of nitrogen, oxygen, sulfur, within the ring wherein, in fused ring systems, one or more the rings can be cycloalkyl, aryl or heteroaryl provided that the point of attachment is through the heterocyclic ring. The sulfur and nitrogen heteroatoms atoms may also be present in their oxidized forms.

The term "substituted heterocycle" or "substituted heterocyclic" or "substituted heterocycloalkyl" refers to heterocycle groups that are substituted with from 1 to 3 of the same substituents as defined for substituted aryl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2, 3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

The term "heterocyclyloxy" as used herein refers to the group —O-heterocyclic.

The term "substituted heterocyclyloxy" as used herein refers to the group-O-substituted heterocyclic.

The term "phosphate" as used herein refers to the groups-OP(O)(OH)$_2$ (monophosphate or phospho), —OP(O)(OH)OP(O)(OH)$_2$ (diphosphate or diphospho) and —OP(O)(OH)OP(O)(OH)OP(O)(OH)$_2$ (triphosphate or triphospho) or salts thereof including partial salts thereof. It is understood that the initial oxygen of the mono-, di-, and triphosphate may include the oxygen atom of a sugar.

The term "phosphate esters" as used herein refers to the mono-, di-, and tri-phosphate groups described above wherein one or more of the hydroxyl groups is replaced by an alkoxy group.

The term "phosphonate" refers to the groups —OP(O)(Z$_4$)(OH) or-OP(O) (Z$_4$)(OZ$_4$) or salts thereof including partial salts thereof, wherein each Z$_4$ is independently selected from hydrogen, alkyl, substituted alkyl, carboxylic acid, and carboxyl ester. It is understood that the initial oxygen of the phosphonate may include the oxygen of a sugar.

The term "thiol" as used herein refers to the group —SH.

The term "thioalkyl" or "alkylthioether" or "thioalkoxy" refers to the group- S-alkyl.

The term "substituted thioalkyl" or "substituted alkylthioether" or "substituted thioalkoxy" refers to the group —S-substituted alkyl.

The term "thiocycloalkyl" as used herein refers to the group —S-cycloalkyl.

The term "substituted thiocycloalkyl" as used herein refers to the group —S-substituted cycloalkyl.

The term "thioaryl" as used herein refers to the group —S-aryl.

The term "substituted thioaryl" as used herein refers to the group-S-substituted aryl.

The term "thioheteroaryl" as used herein refers to the group —S-heteroaryl.

The term "substituted thioheteroaryl" as used herein refers to the group —S-substituted heteroaryl.

The term "thioheterocyclic" as used herein refers to the group —S-heterocyclic.

The term "substituted thioheterocyclic" as used herein refers to the group —S-substituted heterocyclic.

The term "alkylcarbonyl" as used herein refers to the group alkyl-(C═O)—.

The term "alkenylcarbonyl" as used herein refers to the group alkenyl-(C═O)—.

The term "alkoxycarbonyl" as used herein refers to the group alkoxy-(C═O)—.

The term "cycloalkylcarbonyl" as used herein refers to the group cycloalkyl-(C═O)—.

The term "cycloalkoxycarbonyl" as used herein refers to the group cycloalkoxy-(C═O)—.

The term "arylcarbonyl" as used herein refers to the group aryl-(C═O)—.

The term "aryloxycarbonyl" as used herein refers to the group aryloxy-(C═O)—.

The term "heteroarylcarbonyl" as used herein refers to the group heteroaryl-(C═O)—.

The term "heteroaryloxycarbonyl" as used herein refers to the group heteroaryloxy-(C═O)—.

The term "alkylamino" as used herein refers to the group alkyl-NH—.

The term "alkylcarbonyloxy" as used herein refers to the group alkyl-(C═O)—O—.

The term "alkyloxycarbonyl" as used herein refers to the group alkoxy-(C═O)—.

The term "alkylaminocarbonyl" as used herein refers to the group alkyl-NH—(C═O)—.

The term "amino acid sidechain" refers to the $Z_7$ substituent of α-amino acids of the formula $Z_6$NHCH($Z_7$)COOH where $Z_7$ is selected from the group consisting of hydrogen, alkyl, substituted alkyl and aryl and $Z_6$ is hydrogen or together with $Z_7$ and the nitrogen and carbon atoms bound thereto respectively form a heterocyclic ring. In one embodiment, the α-amino acid sidechain is the sidechain one of the twenty naturally occurring L amino acids.

Sugars described herein may either be in D or L configuration.

Compounds of Formula I

In one embodiment the invention provides a compound of the invention, which is a compound of formula I:

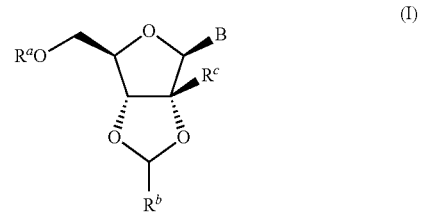

wherein:

B is selected from:

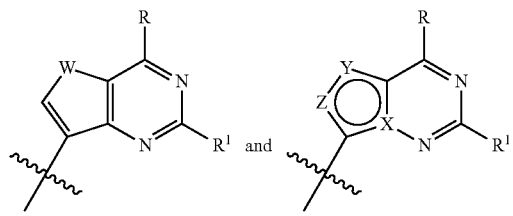

W is O, S, or NH;

X is N, Y is N and Z is CH; or X is N, Y is $CR^{23}$ and Z is CH; or X is C, Y is $CR^{23}$ and Z is O;

R is $OR_3$, $SR_3$, $NR_3R_4$, $NR_3NR_4R_5$, alkyl, substituted alkyl, alkenyl, substituted alkenyl, alkynyl, substituted alkynyl, aryl, substituted aryl, $(CH_2)_n$—CH(NHR$_3$)CO$_2$R$_4$, $(CH_2)_n$—S-alkyl, $(CH_2)_n$—S-aryl, Cl, F, Br, I, CN, COOR$_3$, CONR$_3$R$_4$, NHC(═NR$_3$)NHR$_4$, NR$_3$OR$_4$, NR$_3$NO, NHCONHR$_3$, NR$_3$N═NR$_4$, NR$_3$N═CHR$_4$, NR$_3$C(O)NR$_4$R$_5$, NR$_3$C(S)NR$_4$R$_5$, NR$_3$C(O)OR$_4$, CH═N—OR$_3$, NR$_3$C(═NH)NR$_4$R$_5$, NR$_3$C(O)NR$_4$NR$_5$R$_6$, O—C(O)R$_3$, OC(O)—OR$_3$, ONH—C(O)O-alkyl, ONHC(O)O-aryl, ONR$_3$R$_4$, SNR$_3$R$_4$, S—ONR$_3$R$_4$, or SO$_2$NR$_3$R$_4$; and R$^{23}$ is H, CN, NO$_2$, alkyl, substituted alkyl, alkenyl, substituted alkenyl, alkynyl, substituted alkynyl, CH=CF$_2$, CH(=NR$_3$)OR$_4$, CHO, CH=CH—OCH$_3$, NHCONH$_2$, NHCSNH$_2$, CONR$_3$R$_4$, CSNR$_3$R$_4$, CO$_2$R$_3$, alkoxy, NH$_2$, alkylamino, dialkylamino, halogen, (1,3-oxazol-2-yl), (1,3-oxazol-5-yl), (1,3-thiazol-2-yl), (imidazol-2-yl), (2-oxo[1,3]dithiol-4-yl), (furan-2-yl), (2H[1,2,3]triazol-4-yl), C(=NH)NH$_2$, C(=NH)NHOH, C(=NOH)NH$_2$, acyl, substituted acyl, OR$_3$, C(=NR$_3$)R$_4$, CH=NNR$_3$R$_4$, CH=NOR$_3$, CH(OR$_3$)$_2$, B(OR$_3$)$_2$, C≡C—C(=O)NR$_3$R$_4$, or N(=NHNH$_2$)NHNH$_2$; or R and R$^{23}$ together with atoms to which they are attached may form a cycloalkyl, substituted cycloalkyl, aryl, substituted aryl, heterocycloalkyl, substituted heterocycloalkyl, heteroaryl, or substituted heteroaryl;

n is 0-5;

R$^1$ is H, NR$_3$R$_4$, Cl, F, OR$_3$, SR$_3$, NHCOR$_3$, NHSO$_2$R$_3$, NHCONHR$_3$, CN, alkyl, aryl, ONR$_3$R$_4$, or NR$_3$C(O)OR$_4$;

R$_3$, R$_4$, R$_5$, and R$_6$ are independently selected from the group consisting of H, alkyl, substituted alkyl, alkenyl, substituted alkenyl, alkynyl, substituted alkynyl, cycloalkyl, heterocyclic, aryl, substituted aryl, acyl, substituted acyl, SO$_2$-alkyl and NO; or R$_3$ and R$_4$ together with the nitrogen to which they are attached form a pyrrolidino, piperidino, piperazino, azetidino, morpholino, or thiomorpholino ring; or R$_4$ and R$_5$ together with the nitrogen to which they are attached form a pyrrolidino, piperidino, piperazino, azetidino, morpholino, or thiomorpholino ring;

R$^a$ is selected from the group consisting of hydrogen, C$_{1-16}$ alkylcarbonyl, C$_{2-18}$ alkenylcarbonyl, C$_{1-10}$ alkyloxycarbonyl, C$_{3-6}$ cycloalkylcarbonyl, C$_{3-6}$ cycloalkyloxycarbonyl, arylcarbonyl, aryloxycarbonyl, heteroarylcarbonyl, heteroaryloxycarbonyl, an amino acyl residue of structural formula —C(=O)CH(R$^{11}$)NH—R$^{12}$, or a residue of structural formula: —P(=O)(O—Ar)—NHCH(R$^{13}$)—C(=O)OR$^{14}$, wherein alkylcarbonyl, alkyloxycarbonyl, cycloalkylcarbonyl, and cycloalkyloxycarbonyl are unsubstituted or substituted with one to three substituents independently selected from the group consisting of halogen, hydroxy, carboxy, C$_{1-4}$ alkoxy, amino, C$_{1-4}$ alkylamino, and di (C$_{1-4}$ alkyl)amino and wherein arylcarbonyl, aryloxycarbonyl, heteroarylcarbonyl, and heteroaryloxycarbonyl are unsubstituted or substituted with one to five substituents independently selected from R$^9$;

Ar is phenyl unsubstituted or substituted with one to three substituents independently selected from the group consisting of halogen, C$_{1-4}$ alkyl, C$_{1-4}$ alkoxy, C$_{1-4}$ alkylthio, cyano, nitro, amino, carboxy, trifluoromethyl, C$_{1-4}$ alkylamino, di(C$_{1-4}$ alkyl)amino, C$_{1-4}$ alkylcarbonyl, C$_{1-4}$ alkylcarbonyloxy, and C$_{1-4}$ alkyloxycarbonyl; each R$^9$ is independently selected from the group consisting of halogen, C$_{1-4}$ alkyl, C$_{1-4}$ alkoxy, C$_{1-4}$ alkylthio, C$_{1-4}$ alkylsulfonyl, cyano, nitro, amino, phenyl, carboxy, trifluoromethyl, difluoromethoxy, trifluoromethoxy, C$_{1-4}$ alkylamino, di(C$_{1-4}$ alkyl)amino, C$_{1-4}$ alkylcarbonyl, C$_{1-4}$ alkylcarbonyloxy, and C$_{1-4}$ alkyloxycarbonyl;

R$^{11}$ is hydrogen, C$_{1-5}$ alkyl, or phenyl C$_{0-2}$ alkyl;

R$^{12}$ is hydrogen, C$_{1-4}$ alkyl, C$_{1-4}$ acyl, benzoyl, C$_{1-4}$ alkyloxycarbonyl, phenyl C$_{0-2}$ alkyloxycarbonyl, C$_{1-4}$ alkylaminocarbonyl, phenyl C$_{0-2}$ alkylaminocarbonyl, C$_{1-4}$ alkylsulfonyl, or phenyl C$_{0-2}$ alkylsulfonyl;

R$^{13}$ is hydrogen, C$_{1-5}$ alkyl, phenyl or benzyl; wherein alkyl is unsubstituted or substituted with one substituent selected from the group consisting of hydroxy, methoxy, amino, carboxy, carbamoyl, guanidino, mercapto, methylthio, 1H-imidazolyl, and 1H-indol-3-yl; and wherein phenyl and benzyl are unsubstituted or substituted with one to two substituents independently selected from the group consisting of halogen, hydroxy, and methoxy;

R$^{14}$ is hydrogen, C$_{1-6}$ alkyl, C$_{3-6}$ cycloalkyl, phenyl, or benzyl; wherein alkyl and cycloalkyl are unsubstituted or substituted with one to three substituents independently selected from halogen, hydroxy, carboxy, C$_{1-4}$ alkoxy; and wherein phenyl and benzyl are unsubstituted or substituted with one to three substituents independently selected from halogen, hydroxy, cyano, C$_{1-4}$ alkoxy, and trifluoromethyl; R$^b$ is selected from the group consisting of C$_{1-12}$ alkyl, C$_{3-8}$ cycloalkyl, aryl, and heteroaryl; wherein alkyl and cycloalkyl are unsubstituted or substituted with one to three substituents independently selected from halogen, hydroxy, carboxy, and C$_{1-4}$ alkoxy; and aryl and heteroaryl are unsubstituted or substituted with one to five substituents independently selected from R$^9$; and R$^c$ is selected from the group consisting of hydrogen, alkyl, alkenyl, and alkynyl wherein each alkyl, alkenyl, and alkynyl is optionally substituted with one or more substituents independently selected from halo, amino, hydroxy, and alkoxy;

or a pharmaceutically acceptable salt thereof.

In one specific embodiment of the invention W is O.

In one specific embodiment of the invention W is S.

In one specific embodiment of the invention R is OR$_3$, Cl, SR$_3$, NR$_3$R$_4$, or NR$_3$NR$_4$R$_5$.

In one specific embodiment of the invention R is hydroxy, chloro, methoxy, mercapto, amino, methylamino, isopropylamino, propylamino, ethylamino, dimethylamino, cyclopropylamino, 2-aminoethylamino, 1-(2-hydroxyethyl)hydrazino, hydrazino, 1-methylhydrazino, azetidino, or pyrrolidino.

In one specific embodiment of the invention R$^1$ is H or NR$_3$R$_4$.

In one specific embodiment of the invention R$^{23}$ is H.

In one specific embodiment the invention provides a compound of formula Ia:

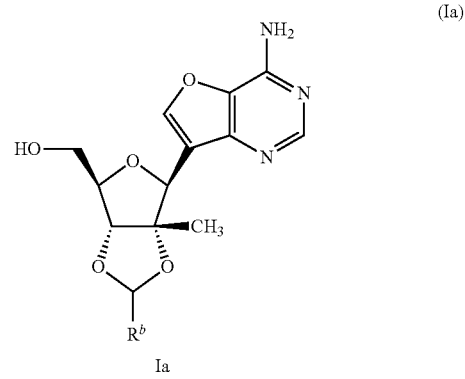

(Ia)

wherein R$^b$ is selected from:

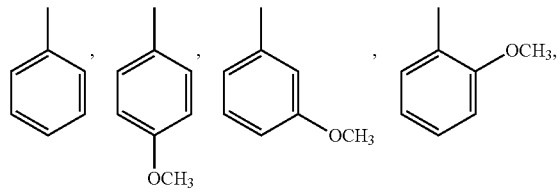

-continued
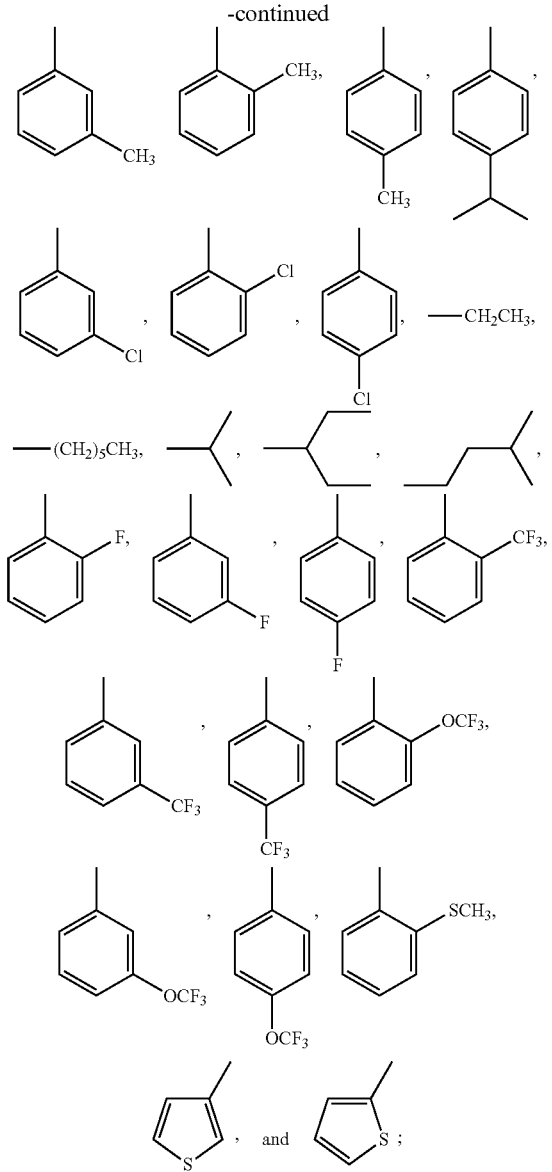
or a pharmaceutically acceptable salt thereof.
In one specific embodiment the invention provides a compound of formula Ib:
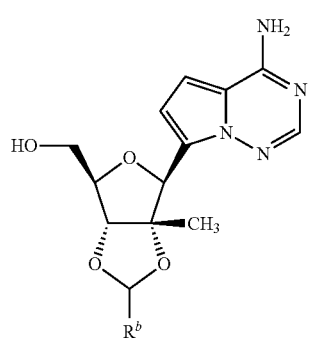
(Ib)
wherein $R^b$ is selected from:
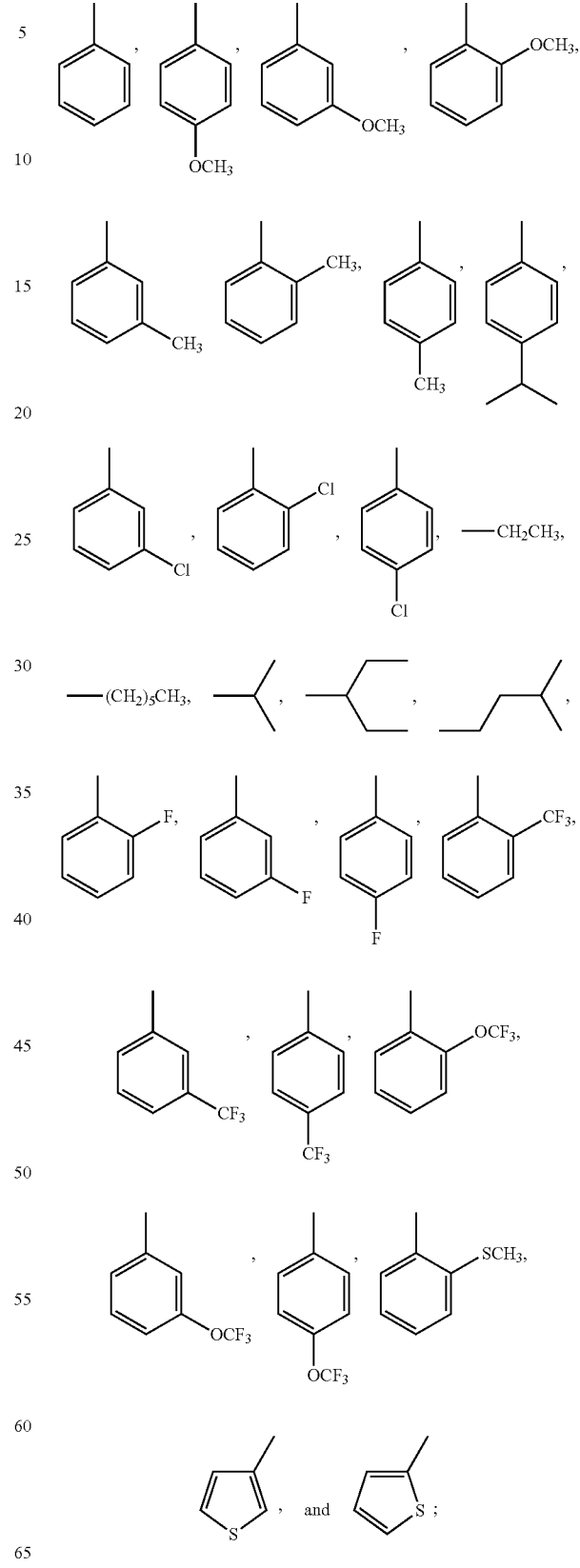
or a pharmaceutically acceptable salt thereof.

In one specific embodiment the invention provides a compound of formula (Ic):

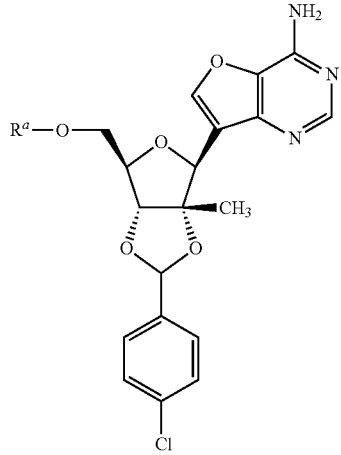

(Ic)

wherein $R^a$ is selected from

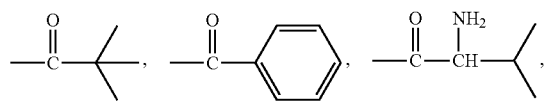

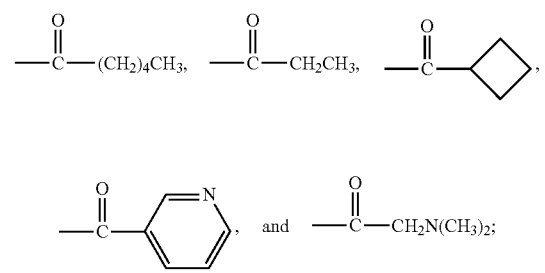

or a pharmaceutically acceptable salt thereof.

In one specific embodiment the invention provides a compound of formula (Id):

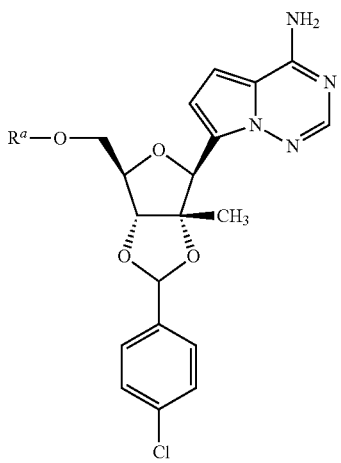

(Id)

wherein $R^a$ is selected from

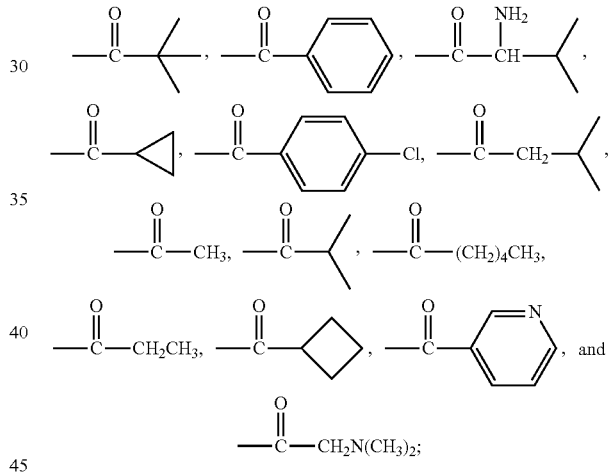

or a pharmaceutically acceptable salt thereof.

In one specific embodiment the invention provides a compound of formula Ie:

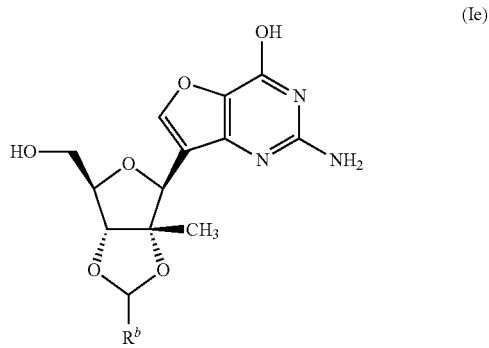

(Ie)

wherein R$^b$ is selected from:
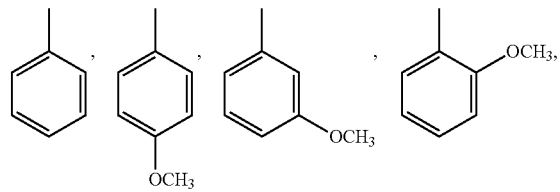
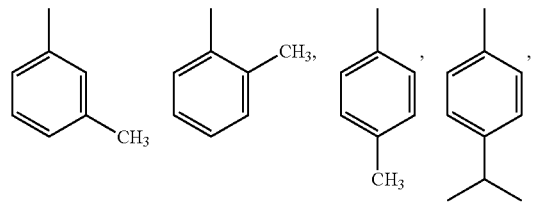
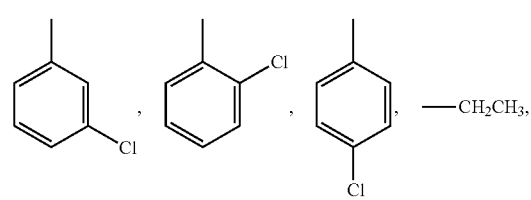
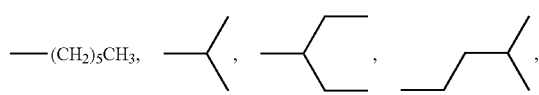
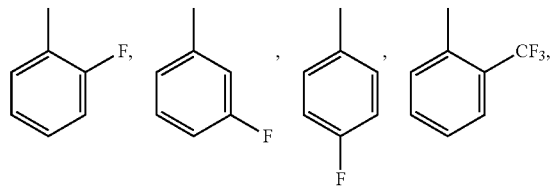
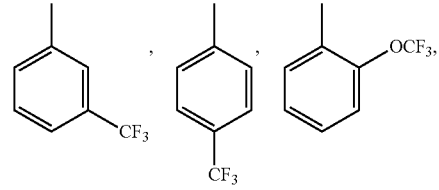
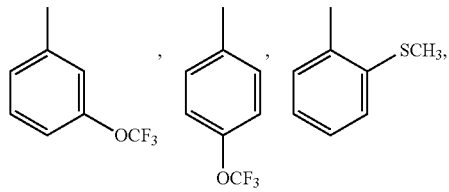
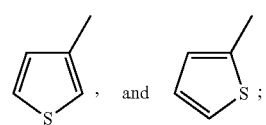
or a pharmaceutically acceptable salt thereof.
In one specific embodiment the invention provides a compound of formula If:
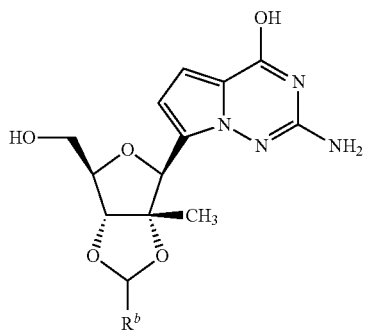
(If)
wherein R$^b$ is selected from:
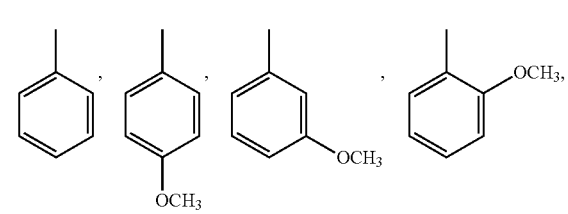
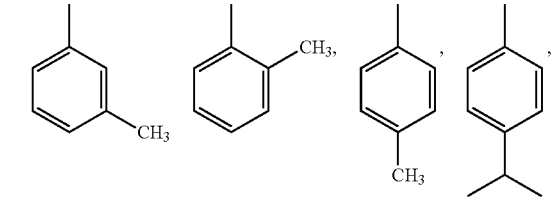
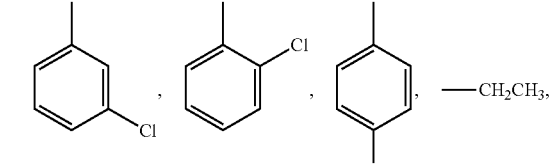
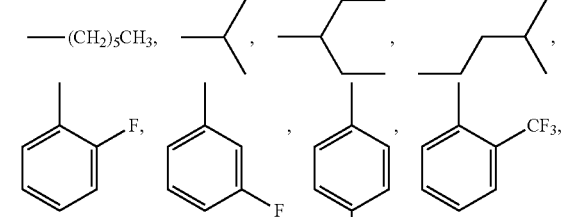
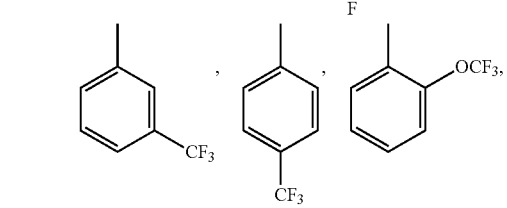
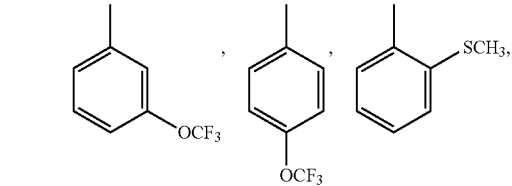

-continued

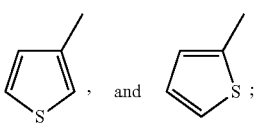

or a pharmaceutically acceptable salt thereof.

In one specific embodiment the invention provides a compound of formula (Ig):

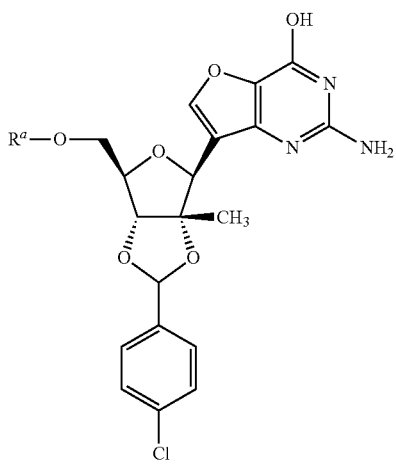

wherein $R^a$ is selected from

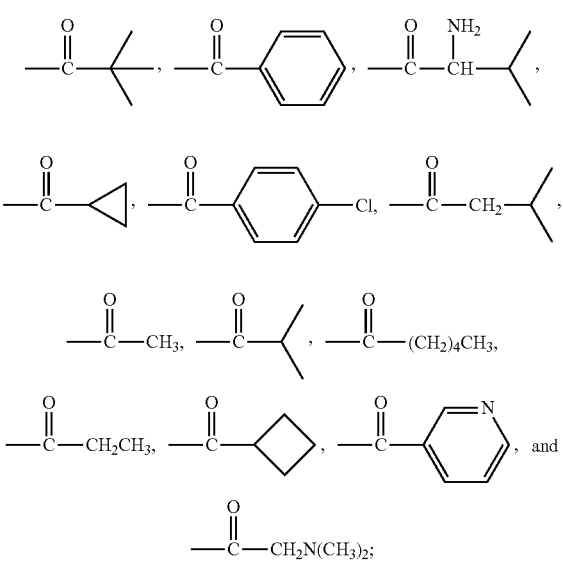

or a pharmaceutically acceptable salt thereof.

In one specific embodiment the invention provides a compound of formula (Ih):

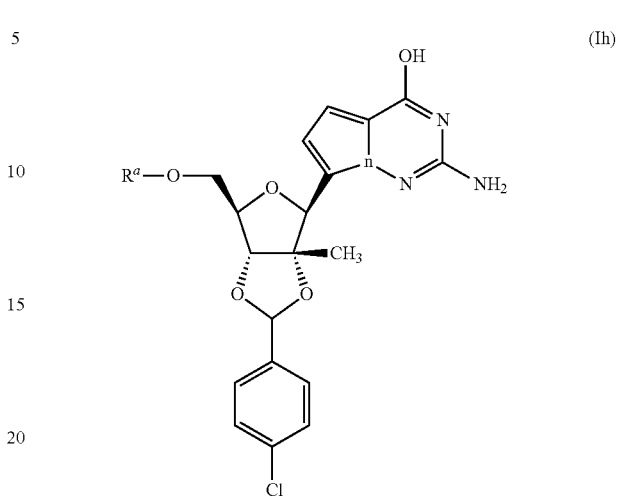

wherein $R^a$ is selected from

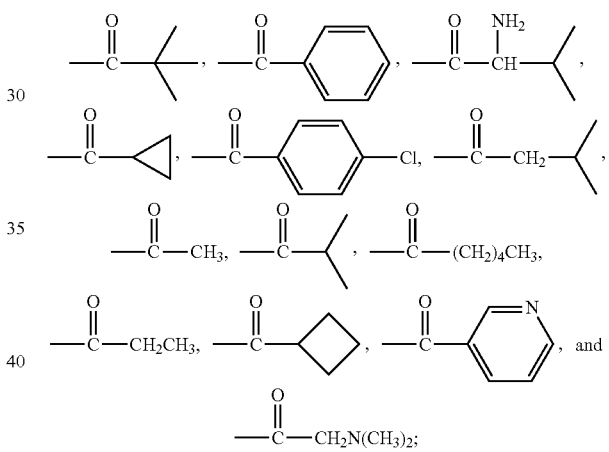

or a pharmaceutically acceptable salt thereof.

Isomers and Physical Forms

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, tautomeric, or stereoisomeric form, or mixtures thereof, of a compound of the invention (e.g. a compound of formula I), which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine anti-viral or anti-cancer activity using the standard tests described herein, or using other similar tests which are well known in the art. Although the invention includes all isomeric forms of the compounds described herein, one embodiment of the invention provides compounds having the absolute stereochemistry depicted in the Examples hereinbelow.

Pharmaceutical Compositions, Modes of Administration and Methods of Treatment

The present disclosure provides compounds of the general formula (I) as detailed above which are inhibitors of DNA and/or RNA viral polymerases and anticancer agents. Various forms of DNA and RNA viral polymerases are inhibited by the compounds disclosed, such as, but not limited to, viral RdRps. The compounds of the present disclosure therefore have utility in treating and/or preventing viral infections in a host and in treatment and/or preventing a variety of disease states and/or conditions caused by or related to such viral infections. In one embodiment, the compounds are useful in the above-mentioned treating and/or preventing by inhibiting viral RNA and DNA polymerases. Such viral agents include, but are not limited to, hepatitis B, hepatitis C, human immunodeficiency virus, Polio, Coxsackie A and B, Rhino, Echo, small pox, Ebola, and West Nile virus. In a particular embodiment, the causative agent of the viral infection is a flavivirus.

The present disclosure provides for a compound of the general formula (I) and a pharmaceutical composition comprising a pharmaceutically effective amount of at least one compound of general formula (I) as described herein. Such compounds and/or pharmaceutical compositions may be used in the manufacture of a medicament for treating and/or preventing a disease or condition in which it is desirable to inhibit viral RNA and DNA polymerases. Such pharmaceutical compositions may also comprise a pharmaceutically acceptable carrier and other ingredients known in the art, or may comprise solely a compound of the general formula (I).

The pharmaceutically acceptable carriers described herein, including, but not limited to, vehicles, adjuvants, excipients, or diluents, are well-known to those who are skilled in the art. Typically, the pharmaceutically acceptable carrier is chemically inert to the active compounds and has no detrimental side effects or toxicity under the conditions of use. The pharmaceutically acceptable carriers can include polymers and polymer matrices.

The compounds described in the instant disclosure can be administered by any conventional method available for use in conjunction with pharmaceuticals, either as individual therapeutic agents or in combination with additional therapeutic agents.

The compounds described are administered in a pharmaceutically effective amount. The pharmaceutically effective amount of the compound and the dosage of the pharmaceutical composition administered will, of course, vary depending upon known factors, such as the pharmacodynamic characteristics of the particular agent and its mode and route of administration; the age, health and weight of the recipient; the severity and stage of the disease state or condition; the kind of concurrent treatment; the frequency of treatment; and the effect desired.

A daily dosage of active ingredient can be expected to be about 0.001 to 1000 milligrams (mg) per kilogram (kg) of body weight per day. In one embodiment, the total amount is between about 0.1 mg/kg and about 100 mg/kg of body weight per day; in an alternate embodiment between about 1.1 mg/kg and about 50 mg/kg of body weight per day; in yet another alternate embodiment between 0.1 mg/kg and about 30 mg/kg of body weight per day. The above described amounts may be administered as a series of smaller doses over a period of time if desired. The pharmaceutically effective amount can be calculated based on the weight of the parent compound to be delivered. If the salt or prodrug exhibits activity in itself, the pharmaceutically effective amount can be estimated as above using the weight of the salt or prodrug, or by other means known to those skilled in the art. The dosage of active ingredient may be given other than daily if desired.

The total amount of the compound administered will also be determined by the route, timing and frequency of administration as well as the existence, nature, and extent of any adverse side effects that might accompany the administration of the compound and the desired physiological effect. It will be appreciated by one skilled in the art that various conditions or disease states, in particular chronic conditions or disease states, may require prolonged treatment involving multiple administrations.

Dosage forms of the pharmaceutical compositions described herein (forms of the pharmaceutical compositions suitable for administration) contain from about 0.1 mg to about 3000 mg of active ingredient (i.e. the compounds disclosed) per unit. In these pharmaceutical compositions, the active ingredient will ordinarily be present in an amount of about 0.5-95% weight based on the total weight of the composition. Multiple dosage forms may be administered as part of a single treatment. The active ingredient may be administered to achieve peak plasma concentrations of the active ingredient of from about 0.2 to 70 $\mu$M, or from about 1.0 to 10 $\mu$M.

The active ingredient can be administered orally in solid dosage forms, such as capsules, tablets, and powders, or in liquid dosage forms, such as elixirs, syrups and suspensions. It can also be administered parenterally, in sterile liquid dosage forms. The active ingredient can also be administered intranasally (nose drops) or by inhalation via the pulmonary system, such as by propellant based metered dose inhalers or dry powder inhalation devices. Other dosage forms are potentially possible such as administration transdermally, via patch mechanisms or ointment.

Formulations suitable for oral administration can include (a) liquid solutions, such as a pharmaceutically effective amount of the compound dissolved in diluents, such as water, saline, or orange juice; (b) capsules, sachets, tablets, lozenges, and troches, each containing a predetermined pharmaceutically effective amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, propylene glycol, glycerin, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, and gels containing, in addition to the active ingredient, such carriers as are known in the art.

Formulations suitable for parenteral administration include aqueous and non-aqueous, isotonic sterile injection solutions, which can contain anti-oxidants, buffers, bacteriostats, and solutes that render the formulation isotonic with the blood of the patient, and aqueous and non-aqueous sterile suspensions that can include suspending agents, solubilizers, thickening agents, stabilizers, and preservatives. The compound can be administered in a physiologically acceptable diluent in a pharmaceutically acceptable carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations, include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyldialkylammonium halides, and alkylpyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl β-aminopropionates, and 2-alkylimidazoline quaternary ammonium salts, and (e) mixtures thereof.

The parenteral formulations typically contain from about 0.5% to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

Pharmaceutically acceptable excipients are also well-known to those who are skilled in the art. The choice of excipient will be determined in part by the particular compound, as well as by the particular method used to administer the composition. Accordingly, there is a wide variety of suitable formulations of the pharmaceutical composition of the present invention. The following methods and excipients are merely exemplary and are in no way limiting. The pharmaceutically acceptable excipients preferably do not interfere with the action of the active ingredients and do not cause adverse side-effects. Suitable carriers and excipients include solvents such as water, alcohol, and propylene glycol, solid absorbents and diluents, surface active agents, suspending agents, tableting binders, lubricants, flavors, and coloring agents.

The compounds of the present invention, alone or in combination with other suitable components, can be made into aerosol formulations to be administered via inhalation. These aerosol formulations can be placed into pressurized acceptable propellants, such as dichlorodifluoromethane, propane, and nitrogen. Such aerosol formulations may be administered by metered dose inhalers. They also may be formulated as pharmaceuticals for non-pressured preparations, such as in a nebulizer or an atomizer.

The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets. The requirements for effective pharmaceutically acceptable carriers for injectable compositions are well known to those of ordinary skill in the art. See Pharmaceutics and Pharmacy Practice, J.B. Lippincott Co., Philadelphia, Pa., Banker and Chalmers, Eds., 238-250 (1982) and ASHP Handbook on Injectable Drugs, Toissel, 4th ed., 622-630 (1986).

Formulations suitable for topical administration include pastilles comprising the active ingredient in an inert base, such as gelatin and glycerin, or sucrose and acacia, as well as creams, emulsions, and gels containing, in addition to the active ingredient, such carriers as are known in the art. Furthermore, transdermal patches can be prepared using methods known in the art.

Additionally, formulations suitable for rectal administration may be presented as suppositories by mixing with a variety of bases such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

One skilled in the art will appreciate that suitable methods of administering a compound of the present invention to a patient are available, and, although more than one route can be used to administer a particular compound, a particular route can provide a more immediate and more effective reaction than another route.

Useful embodiments of pharmaceutical dosage forms for administration of the compounds according to the present invention can be illustrated as follows.

A large number of hard-shell capsules are prepared by filling standard two-piece hard gelatin capsules each with 100 mg of powdered active ingredient, 150 mg of lactose, 50 mg of cellulose and 6 mg of magnesium stearate.

A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

A large number of tablets are prepared by conventional procedures so that the dosage unit is 100 mg of active ingredient, 0.2 mg of colloidal silicon dioxide, 5 mg of magnesium stearate, 275 mg of microcrystalline cellulose, 11 mg of starch, and 98.8 mg of lactose. Appropriate aqueous and non-aqueous coatings may be applied to increase palatability, improve elegance and stability or delay absorption.

Immediate release tablets/capsules are solid oral dosage forms made by conventional and novel processes. These units are taken orally without water for immediate dissolution and delivery of the medication. The active ingredient is mixed in a liquid containing ingredients such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Moreover, the compounds of the present invention can be administered in the form of nose drops, or metered dose and a nasal or buccal inhaler. The drug is delivered from a nasal solution as a fine mist or from a powder as an aerosol.

In one embodiment, the teachings of the present disclosure provide for the use of such pharmaceutical compositions and medicaments in a method of treating a viral infection or treating a disease state and/or condition caused by or related to such viral infection. In one embodiment, the treatment is the result of the inhibition of a viral RNA or DNA polymerase, such as, but not limited to, a RdRp. Such treatment or inhibition need not be complete to be useful. The method of treatment comprises the steps of: (i) identifying a patient in need of such treatment; (ii) providing such pharmaceutical composition containing at least one compound of the invention; and (iii) administering such pharmaceutical composition in a pharmaceutically effective amount to treat the viral infection in a patient in need of such treatment or to inhibit the activity of a viral RNA or DNA polymerase in a patient in need of such treatment.

In one embodiment, the teachings of the present disclosure provide for the use of such pharmaceutical compositions and medicaments in a method of preventing or suppressing a viral infection or preventing or suppressing a disease state and/or condition caused by or related to such viral infection. In one embodiment, the prevention or suppression is the result of the inhibition of a viral RNA or DNA polymerase, such as, but not limited to, a RdRp. Such prevention, suppression or inhibition need not be complete to be useful. The method of preventing or suppressing comprises the steps of: (i) identifying a patient in need of such prevention; (ii) providing such pharmaceutical composition containing at least one compound of the general formula (I); and (iii) administering such pharmaceutical composition in a pharmaceutically effective amount to prevent or suppress the viral infection in a patient in need of such treatment or to inhibit the activity of a viral RNA and DNA polymerase in a patient in need of such treatment.

The methods of the treating and preventing a viral infection or a disease state and/or condition caused by or related to said viral infection may further comprise administering a pharmaceutically effective amount of a compound of the present invention in combination with a pharmaceutically effective amount of another anti-viral agent which, in particular, may be active against HCV. Agents active against HCV include, but are not limited to, ribavirin, levovirin, viramidine, thymosin alpha-1, an inhibitor of HCV NS3 serine protease, an inhibitor of inosine monophosphatedehydrognease, interferon-α, pegylated interferon-α (peginterferon-α), a combination of interferon-α and ribavirin, a combination of peginterferon-αand ribavirin, a combination of interferon-αand levovirin, and a combination of peginterferon-αand levovirin. Interferon-α includes, but is not limited to, recombinant interferon-α2a, interferon-α2b, a consensus interferon, and a purified interferon-α product.

The compounds and pharmaceutical compositions of the present disclosure can be administered to patients to prevent and/or treat a number of cancers. Cancers include, but are not limited to, leukemias and lymphomas such as acute lymphocytic leukemia, acute nonlymphocytic leukemias, chronic lymphocytic leukemia, chronic myelogenous leukemia, Hodgkin's Disease, non-Hodgkin'lymphomas, and multiple myeloma, childhood solid tumors such as brain tumors, neuroblastoma, retinoblastoma, Wilms Tumor, bone tumors, and soft-tissue sarcomas, common solid tumors of adults such as lung cancer, colon and rectum cancer, breast cancer, prostate cancer, urinary cancers, uterine cancers, oral cancers, pancreatic cancer, melanoma and other skin cancers, stomach cancer, ovarian cancer, brain tumors, liver cancer, laryngeal cancer, thyroid cancer, esophageal cancer, and testicular cancer. The cancer may be related to a viral infection or an activity of a viral DNA or RNA polymerase.

The methods of the treating and preventing cancer may also comprise further administering of an anti-cancer agent in combination with any of the compounds or pharmaceutical compositions of the present disclosure. Any suitable chemotherapeutic agent can be employed for this purpose. The chemotherapeutic agent is typically selected from the group consisting of alkylating agents, antimetabolites, natural products, hormonal agents, and miscellaneous agents.

Examples of alkylating chemotherapeutic agents include carmustine, chlorambucil, cisplatin, lomustine, cyclophosphamide, melphalan, mechlorethamine, procarbazine, thiotepa, uracil mustard, triethylenemelamine, busulfan, pipobroman, streptozocin, ifosfamide, dacarbazine, carboplatin, and hexamethylmelamine.

Examples of chemotherapeutic agents that are antimetabolites include cytosine arabinoside, fluorouracil, gemcitabine, hydroxyurea, mercaptopurine, methotrexate, azaserine, thioguanine, floxuridine, fludarabine, cladribine and L-asparaginase.

Examples of chemotherapeutic agents that are natural products include actinomycin D, bleomycin, camptothecins, daunomycin, doxorubicin, etoposide, mitomycin C, TAXOL™ (paclitaxel), taxotere, teniposide, vincristine, vinorelbine, mithramycin, idarubicin, MITHRACIN™ (plicamycin), and deoxycoformycin.

An example of a hormonal chemotherapeutic agent includes tamoxifen. Examples of the aforesaid miscellaneous chemotherapeutic agents include mitotane, mitoxantrone, vinblastine, and levamisole.

The ability of a compound to inhibit viral polymerases can be evaluated using known assays. The ability of a compound to inhibit HCV NS5B polymerase can be evaluated using the following assay.

HCV NS5B Polymerase Assay

A representative prodrug (see Example 1) of the invention has been tested in vivo and hydrolyzes in vivo to provide an active compound.

Antiviral activity of the compounds can be assessed (Okuse et al., Antiviral Res. 2005, 65, 23-34) in the stably HCV RNA-replicating cell line, AVA5, derived by transfection of the human hepatoblastoma cell line, Huh7 (Blight et al., Sci. 2000, 290, 1972). Compounds are added to dividing cultures once daily for three days. Media is changed with each addition of compound. Cultures generally start the assay at 30-50% confluence and reach confluence during the last day of treatment. Intracellular HCV RNA levels and cytotoxicity are assessed 24 hours after the last dose of compound.

Triplicate cultures for HCV RNA levels (on 48-well and 96-well plates) and cytotoxicity (on 96-well plates) are used. A total of six untreated control cultures, and triplicate cultures treated with a-interferon and ribavirin serve as positive antiviral and toxicity controls.

Intracellular HCV RNA levels are measured using a conventional blot hybridization method in which HCV RNA levels are normalized to the levels of B-actin RNA in each individual culture (Okuse et al., Antivir. Res. 2005, 65, 23-34). Cytotoxicity is measured using a neutral red dye uptake assay (Korba and Gerin, Antivir. Res. 1992, 19, 55). HCV RNA levels in the treated cultures are expressed as a percentage of the mean levels of RNA detected in untreated cultures.

Compound Synthesis

Compound of formula I can be prepared using synthetic intermediates and synthetic procedures that are known (for example, see PCT/US2005/039072 and PCT/US2006/030549), or they can be prepared using the synthetic intermediates and synthetic procedures identified in Schemes A1-C2, and the accompanying Examples herein.

Preparation of $R^2$—$CH_2CN$ Compounds:

-continued

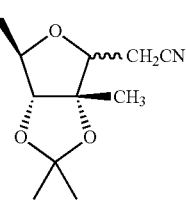

R = tert-butyldiphenylsilyl

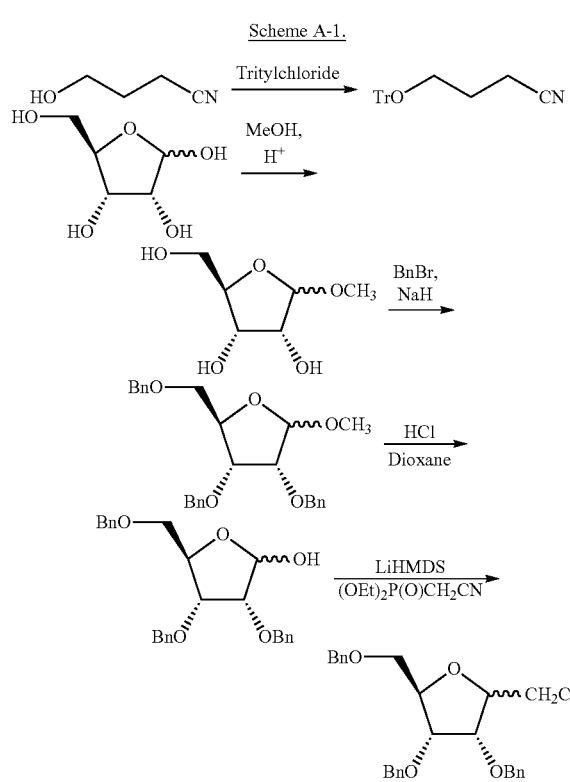

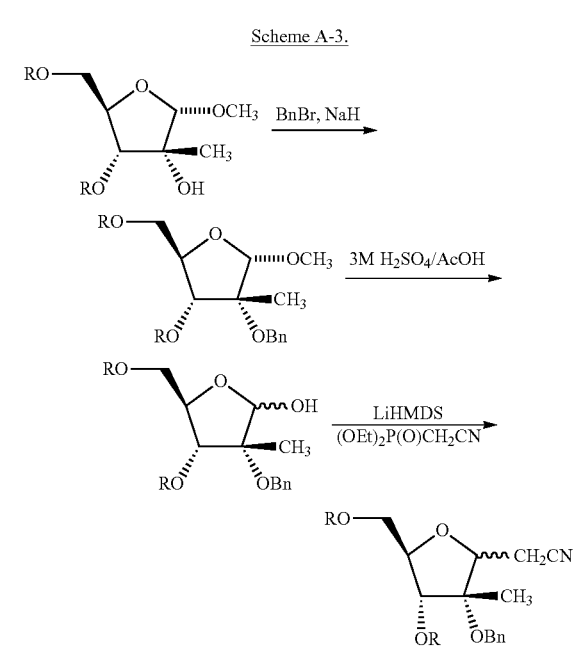

R = 2,4-dichlorobenzyl

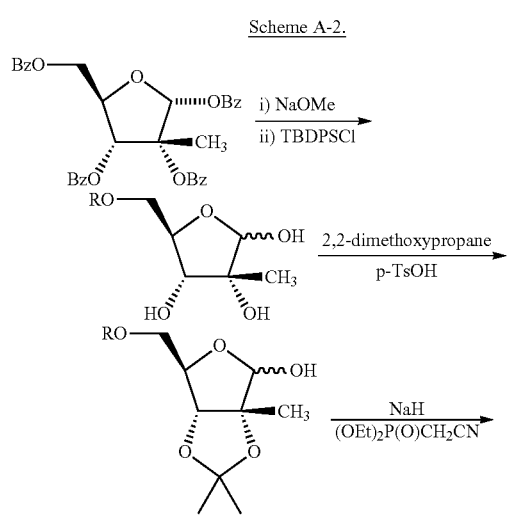

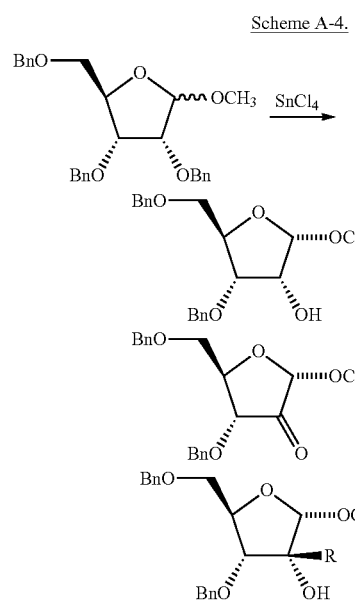

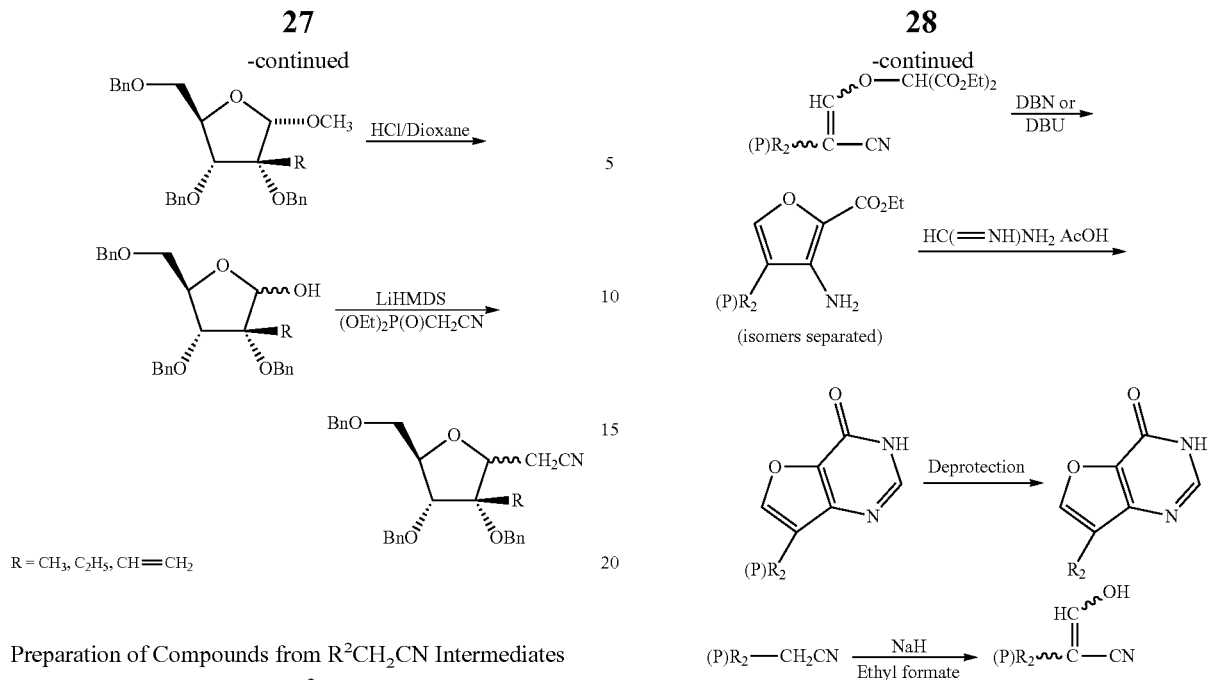
Preparation of Compounds from $R^2CH_2CN$ Intermediates
In the following schemes, $R^2$ is a nucleoside sugar group (e.g. a substituted tetrahydrofuranyl. $(P)R^2$ is a nucleoside sugar group bearing one or more protecting groups.
Scheme B-1.
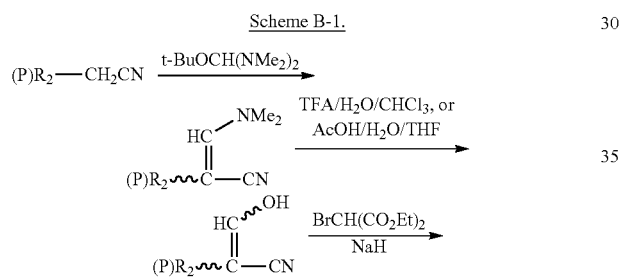
Scheme B-2.
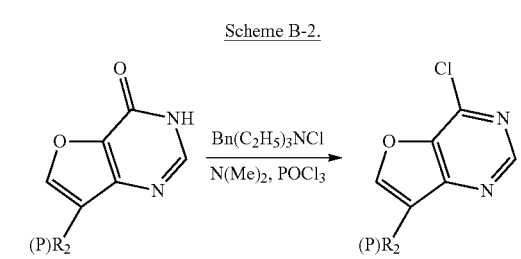
Scheme B-3.
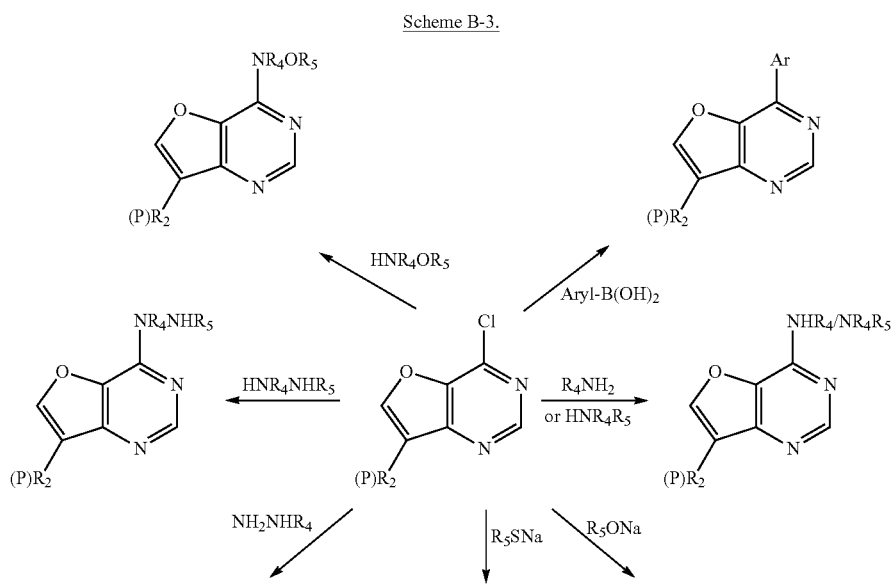

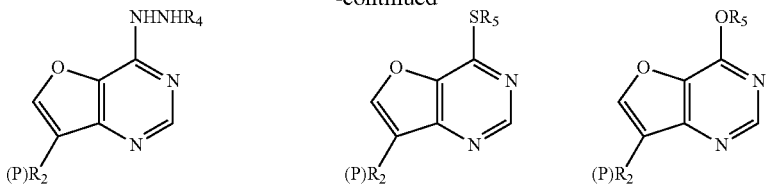
Deprotection of protecting groups in $R_2$ gives the target molecules
$NR_4R_5$ = Azetidine, pyrrolidine
$R_4, R_5$ = H, $CH_3$, $C_2H_5$, n-$C_3H_7$, i-$C_3H_7$, ◁, $CH_2CH_2OH$, $CH_2CH_2NH_2$, $NH_2(CH_2)_nNH_2$
Scheme B-4.
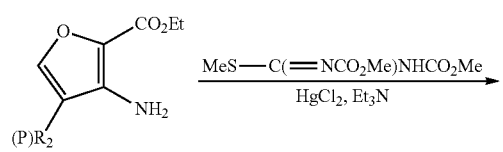
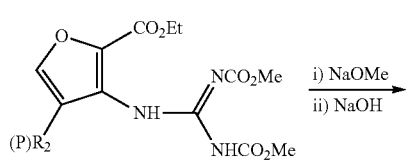
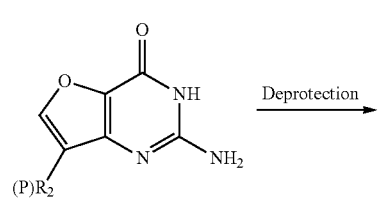
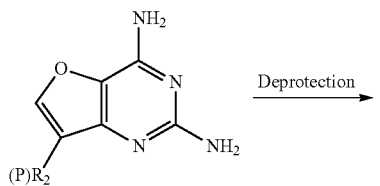
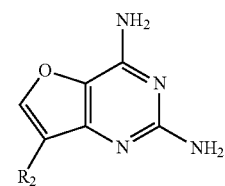
Scheme B-5.
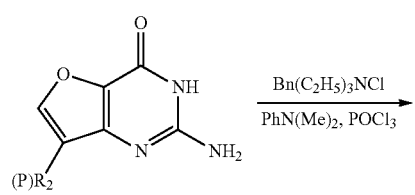
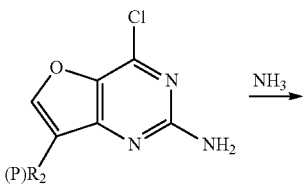
Scheme B-6.
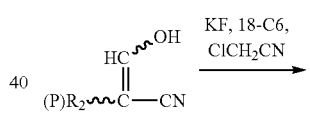
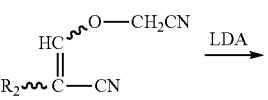
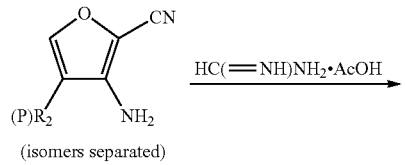
(isomers separated)
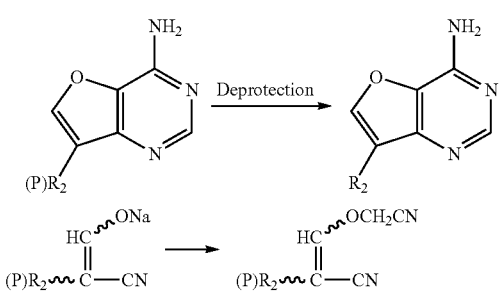

Scheme B-7.
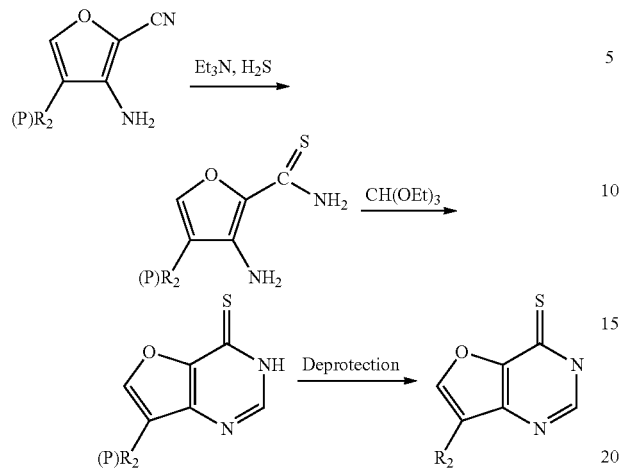
Scheme B-8.
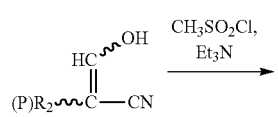
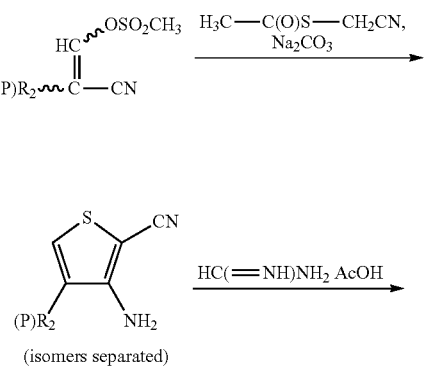
Scheme B-9.
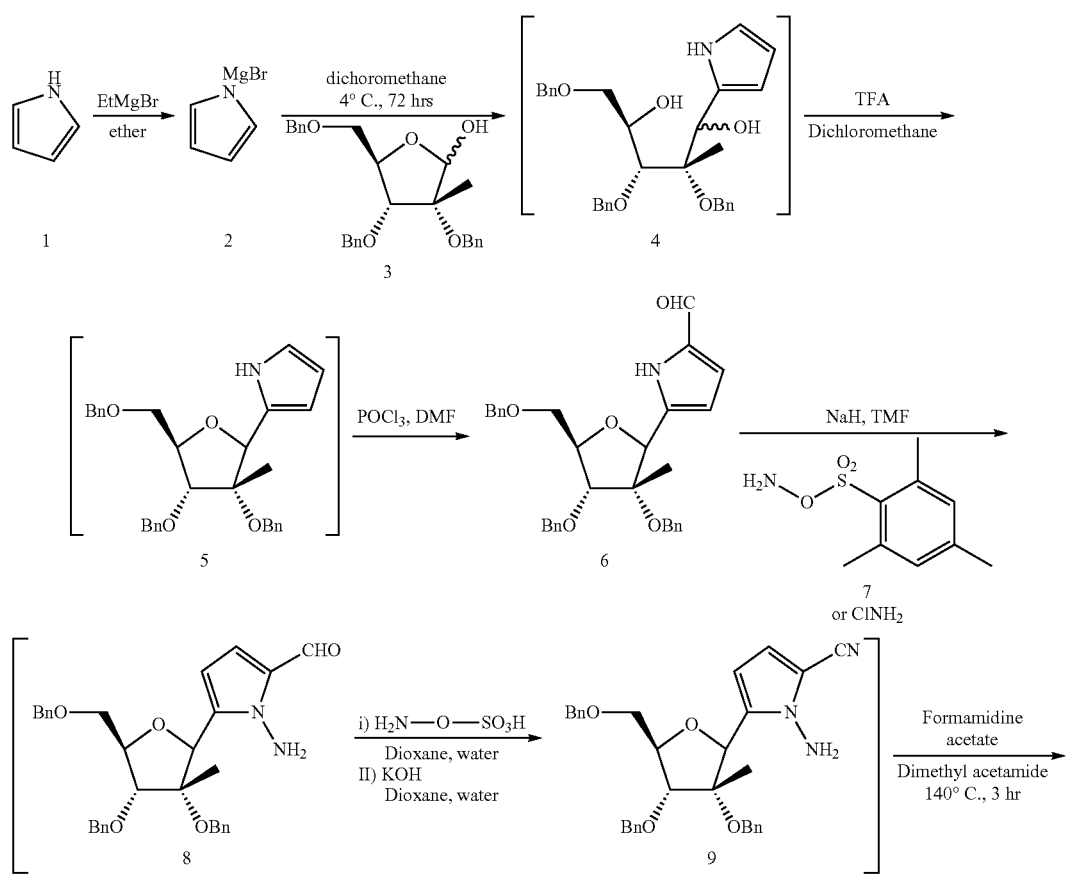

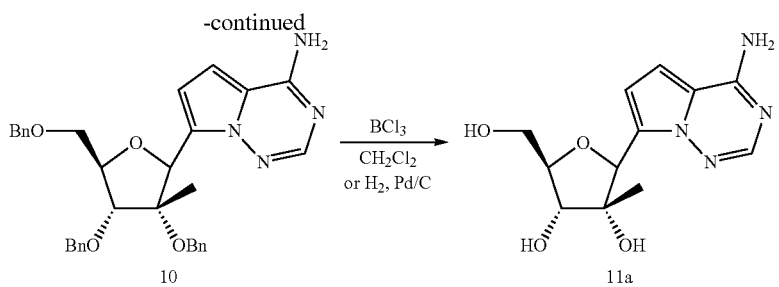

Scheme B-9

The nitrile group of compound 9 in Scheme B-9 is converted to the corresponding amide and then cyclized with triethylorthoformate to give the corresponding hypoxanthine derivative. The hypoxanthine derivative is converted to the 6-chloro derivative and then to various 6-substituted derivatives as illustrated in Scheme B-3.

The nitrile group of compound 9 in Scheme B-9 also is converted to an ester and subsequently to the corresponding guanine analog as illustrated in Scheme B-4.

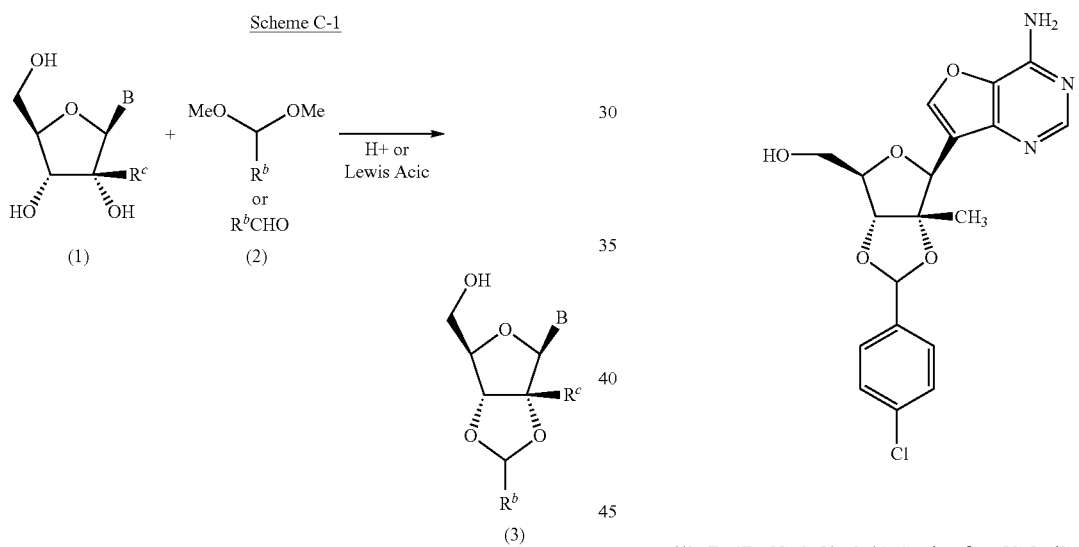

Scheme C-1
The reaction of nucleoside (1) with corresponding aldehyde or diacetal of aldehyde (2) in the presence of acid such as p-toluenesulfonic acid or Lewis acid such as zinc chloride generates the desired compound (3).

Scheme C-2

Further compound (3) reacts with an acid chloride or acid anhydride in the presence of DMAP to generate the target (5) wherein Ra is linked through a carbonyl group.

The invention will now be illustrated by the following non-limiting Examples.

EXAMPLE 1

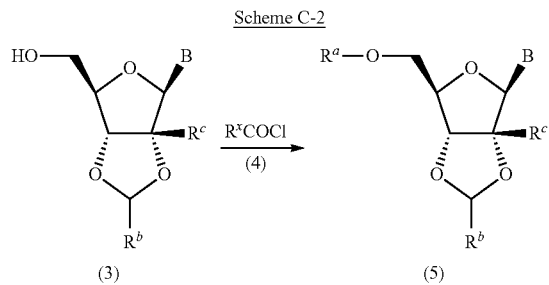

((3aR,4R,6S,6aS)-6-(4-Aminofuro[3,2-d]pyrimidin-7-yl)-2-(4-chlorophenyl)-6a-methyltetrahydrofuro[3,4-d][1,3]dioxol-4-yl)methanol A suspension of (2S,3R,4R,5R)-2-(4-aminofuro[3,2-d]pyrimidin-7-yl)-5-(hydroxymethyl)-3-methyl-tetrahydrofuran-3,4-diol (281 mg, 1.0 mmol) in THF (4 mL) was treated with $ZnCl_2$ (695 mg, 98%, 5 0 mmol) and 4-chlorobenzaldehyde (1.43 g, 10.0 mmol) followed by stirring at 60° C. for 14 h. The reaction mixture was quenched with aqueous 2N NaOH (6.5 mL) followed by dilution with water (80 mL), and extraction with $CHCl_3$ (2×100 mL). The combined organic extracts were dried over $MgSO_4$, filtered, and concentrated. The residue was purified on a silica gel column using chloroform/MeOH (1:0 to 20:1, $R_f$=0.31, $CHCl_3$/MeOH=20:1) as eluent to give 224 mg (55%) of the desired product as a white solid. $^1$H NMR (MeOH-$d_4$, a mixture of diastereoisomers): δ 8.23 (s, 1H), 8.22 (s, 1H), 7.72-7.50 (m, 4H), 7.44 (s, 2H), 6.16 (s, 1H), 5.47-5.41(m, 1H), 5.31 (s, 1H), 4.53 (d, J=3.1 Hz, 1H), 4.17-4.11 (m, 1H), 3.73-3.57 (m, 2H), 1.25 (s, 3H); MS (ES$^+$): 404.3 (M+H)$^+$.

This compound hydrolyzes in vivo to provide an active compound.

Other compounds of formula I can be prepared from the appropriate starting materials using methods similar to those described herein.

EXAMPLE 2

The following illustrate representative pharmaceutical dosage forms, containing a compound of formula I, or a pharmaceutically acceptable salt thereof ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution | q.s. |
| (pH adjustment to 7.0-7.5) | |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 01 N Sodium hydroxide solution | q.s. |
| (pH adjustment to 7.0-7.5) | |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed:
1. A compound of formula I:

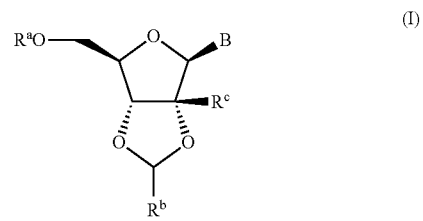

wherein:
B is selected from:

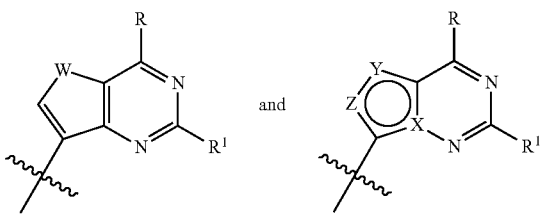

W is O, S, or NH;
X is N, Y is N and Z is CH; or X is N, Y is $CR^{23}$ and Z is CH; or X is C, Y is $CR^{23}$ and Z is O;
R is $OR_3$, $SR_3$, $NR_3R_4$, $NR_3NR_4R_5$, alkyl, substituted alkyl, alkenyl, substituted alkenyl, alkynyl, substituted alkynyl, aryl, substituted aryl, $(CH_2)_n$—CH(NHR_3)$CO_2R_4$, $(CH_2)_n$—S-alkyl, $(CH_2)_n$—S-aryl, Cl, F, Br, I, CN, $COOR_3$, $CONR_3R_4$, NHC(=$NR_3$)$NHR_4$, $NR_3OR_4$, $NR_3NO$, $NHCONHR_3$, $NR_3N$=$NR_4$, $NR_3N$=$CHR_4$, $NR_3C(O)NR_4R_5$, $NR_3C(S)NR_4R_5$, $NR_3C(O)OR_4$, CH=N—$OR_3$, $NR_3C$(=NH)$NR_4R_5$, $NR_3C(O)NR_4NR_5R_6$, O—C(O)$R_3$, OC(O)—$OR_3$, ONH—C(O)O-alkyl, ONHC(O)O-aryl, $ONR_3R_4$, $SNR_3R_4$, S—$ONR_3R_4$, or $SO_2NR_3R_4$; and $R^{23}$ is H, CN, $NO_2$, alkyl, substituted alkyl, alkenyl, substituted alkenyl, alkynyl, substituted alkynyl, CH=$CF_2$, CH(=$NR_3$)$OR_4$, CHO, CH=CH—$OCH_3$, $NHCONH_2$, $NHCSNH_2$, $CONR_3R_4$, $CSNR_3R_4$, $CO_2R_3$, alkoxy, $NH_2$, alkylamino, dialkylamino, halogen, (1,3-oxazol-2-yl), (1,3-oxazol-5-yl), (1,3-thiazol-2-yl), (imidazol-2-yl), (2-oxo[1,3]dithiol-4-yl), (furan-2-yl), (2H[1,2,3]triazol-4-yl), C(=NH)$NH_2$, C(=NH)NHOH, C(=NOH)$NH_2$, acyl, substituted acyl, $OR_3$, C(=$NR_3$)$R_4$, CH=$NNR_3R_4$, CH=$NOR_3$, CH($OR_3$)$_2$, B($OR_3$)$_2$, C≡C—C(=O)$NR_3R_4$, or N(=$NHNH_2$)$NHNH_2$; or R and $R^{23}$ together with atoms to which they are attached may form a cycloalkyl, substituted cycloalkyl, aryl, substituted aryl, heterocycloalkyl, substituted heterocycloalkyl, heteroaryl, or substituted heteroaryl;
n is 0-5;
$R^1$ is H, $NR_3R_4$, Cl, F, $OR_3$, $SR_3$, $NHCOR_3$, $NHSO_2R_3$, $NHCONHR_3$, CN, alkyl, aryl, $ONR_3R_4$, or $NR_3C(O)OR_4$;

$R_3$, $R_4$, $R_5$, and $R_6$ are independently selected from the group consisting of H, alkyl, substituted alkyl, alkenyl, substituted alkenyl, alkynyl, substituted alkynyl, cycloalkyl, heterocyclic, aryl, substituted aryl, acyl, substituted acyl, $SO_2$-alkyl and NO; or $R_3$ and $R_4$ together with the nitrogen to which they are attached form a pyrrolidino, piperidino, piperazino, azetidino, morpholino, or thiomorpholino ring; or $R_4$ and $R_5$ together with the nitrogen to which they are attached form a pyrrolidino, piperidino, piperazino, azetidino, morpholino, or thiomorpholino ring;

$R^a$ is selected from the group consisting of hydrogen, $C_{1-16}$ alkylcarbonyl, $C_{2-18}$ alkenylcarbonyl, $C_{1-10}$ alkyloxycarbonyl, $C_{3-6}$ cycloalkylcarbonyl, $C_{3-6}$ cycloalkyloxycarbonyl, arylcarbonyl, aryloxycarbonyl, heteroarylcarbonyl, heteroaryloxycarbonyl, an amino acyl residue of structural formula —C(=O)CH($R^{11}$)NH—$R^{12}$, or a residue of structural formula: —P(=O)(O—Ar)—NHCH($R^{13}$)—C(=O)O$R^{14}$, wherein alkylcarbonyl, alkyloxycarbonyl, cycloalkylcarbonyl, and cycloalkyloxycarbonyl are unsubstituted or substituted with one to three substituents independently selected from the group consisting of halogen, hydroxy, carboxy, $C_{1-4}$ alkoxy, amino, $C_{1-4}$ alkylamino, and di ($C_{1-4}$ alkyl) amino and wherein arylcarbonyl, aryloxycarbonyl, heteroarylcarbonyl, and heteroaryloxycarbonyl are unsubstituted or substituted with one to five substituents independently selected from $R^9$;

Ar is phenyl unsubstituted or substituted with one to three substituents independently selected from the group consisting of halogen, $C_{1-4}$ alkyl, $C_{1-4}$ alkoxy, $C_{1-4}$ alkylthio, cyano, nitro, amino, carboxy, trifluoromethyl, $C_{1-4}$ alkylamino, di($C_{1-4}$ alkyl)amino, $C_{1-4}$ alkylcarbonyl, $C_{1-4}$ alkylcarbonyloxy, and $C_{1-4}$ alkyloxycarbonyl;

each $R^9$ is independently selected from the group consisting of halogen, $C_{1-4}$ alkyl, $C_{1-4}$ alkoxy, $C_{1-4}$ alkylthio, $C_{1-4}$ alkylsulfonyl, cyano, nitro, amino, phenyl, carboxy, trifluoromethyl, difluoromethoxy, trifluoromethoxy, $C_{1-4}$ alkylamino, di($C_{1-4}$ alkyl)amino, $C_{1-4}$ alkylcarbonyl, $C_{1-4}$ alkylcarbonyloxy, and $C_{1-4}$ alkyloxycarbonyl;

$R^{11}$ is hydrogen, $C_{1-5}$ alkyl, or phenyl $C_{0-2}$ alkyl;

$R^{12}$ is hydrogen, $C_{1-4}$ alkyl, $C_{1-4}$ acyl, benzoyl, $C_{1-4}$ alkyloxycarbonyl, phenyl $C_{0-2}$ alkyloxycarbonyl, $C_{1-4}$ alkylaminocarbonyl, phenyl $C_{0-2}$ alkylaminocarbonyl, $C_{1-4}$ alkylsulfonyl, or phenyl $C_{0-2}$ alkylsulfonyl;

$R^{13}$ is hydrogen, $C_{1-5}$ alkyl, phenyl or benzyl; wherein alkyl is unsubstituted or substituted with one substituent selected from the group consisting of hydroxy, methoxy, amino, carboxy, carbamoyl, guanidino, mercapto, methylthio, 1H-imidazolyl, and 1H-indol-3-yl; and wherein phenyl and benzyl are unsubstituted or substituted with one to two substituents independently selected from the group consisting of halogen, hydroxy, and methoxy;

$R^{14}$ is hydrogen, $C_{1-6}$ alkyl, $C_{3-6}$ cycloalkyl, phenyl, or benzyl; wherein alkyl and cycloalkyl are unsubstituted or substituted with one to three substituents independently selected from halogen, hydroxy, carboxy, $C_{1-4}$ alkoxy; and wherein phenyl and benzyl are unsubstituted or substituted with one to three substituents independently selected from halogen, hydroxy, cyano, $C_{1-4}$ alkoxy, and trifluoromethyl;

$R^b$ is selected from the group consisting of $C_{1-12}$ alkyl, $C_{3-8}$ cycloalkyl, aryl, and heteroaryl; wherein alkyl and cycloalkyl are unsubstituted or substituted with one to three substituents independently selected from halogen, hydroxy, carboxy, and $C_{1-4}$ alkoxy; and aryl and heteroaryl are unsubstituted or substituted with one to five substituents independently selected from $R^9$; and $R^c$ is selected from the group consisting of hydrogen, alkyl, alkenyl, and alkynyl wherein each alkyl, alkenyl, and alkynyl is optionally substituted with one or more substituents independently selected from halo, amino, hydroxy, and alkoxy;

or a pharmaceutically acceptable salt thereof.

2. The compound of claim 1 wherein W is O.

3. The compound of claim 1 wherein W is S.

4. The compound of claim 1 wherein R is O$R_3$, Cl, S$R_3$, N$R_3R_4$, or N$R_3$N$R_4R_5$.

5. The compound of claim 1 wherein R is hydroxy, chloro, methoxy, mercapto, amino, methylamino, isopropylamino, propylamino, ethylamino, dimethylamino, cyclopropylamino, 2-aminoethylamino, 1-(2-hydroxyethyl)hydrazino, hydrazino, 1-methylhydrazino, azetidino, or pyrrolidino.

6. The compound of claim 1 wherein $R^1$ is H or N$R_3R_4$.

7. A compound of formula Ia:

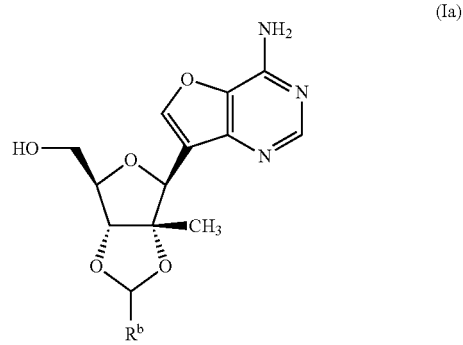

wherein $R^b$ is selected from:

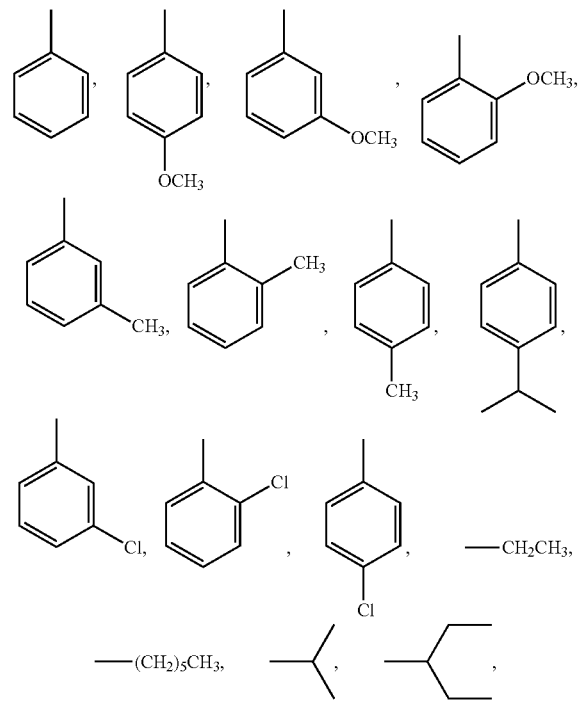

-continued
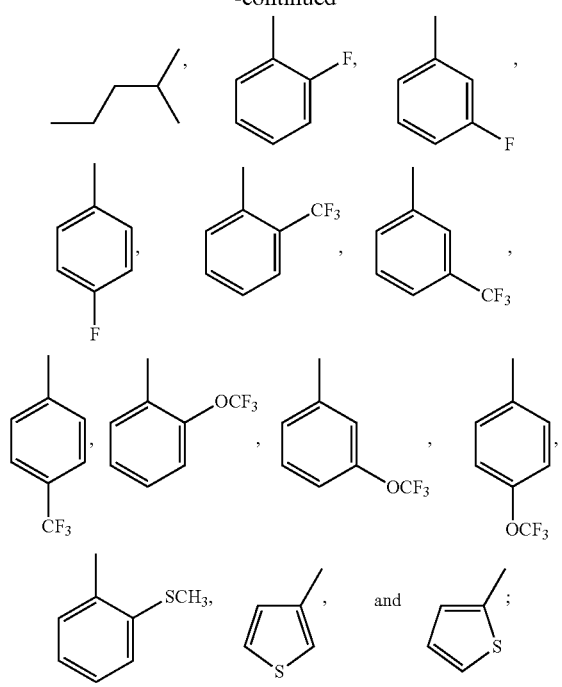
or a pharmaceutically acceptable salt thereof.
8. A compound of formula Ib:
(Ib)
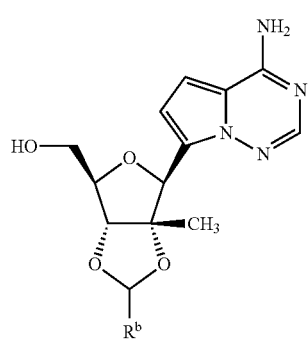
wherein $R^b$ is selected from:
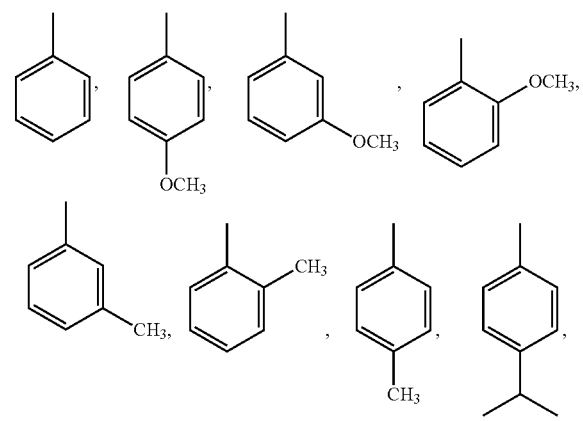
-continued
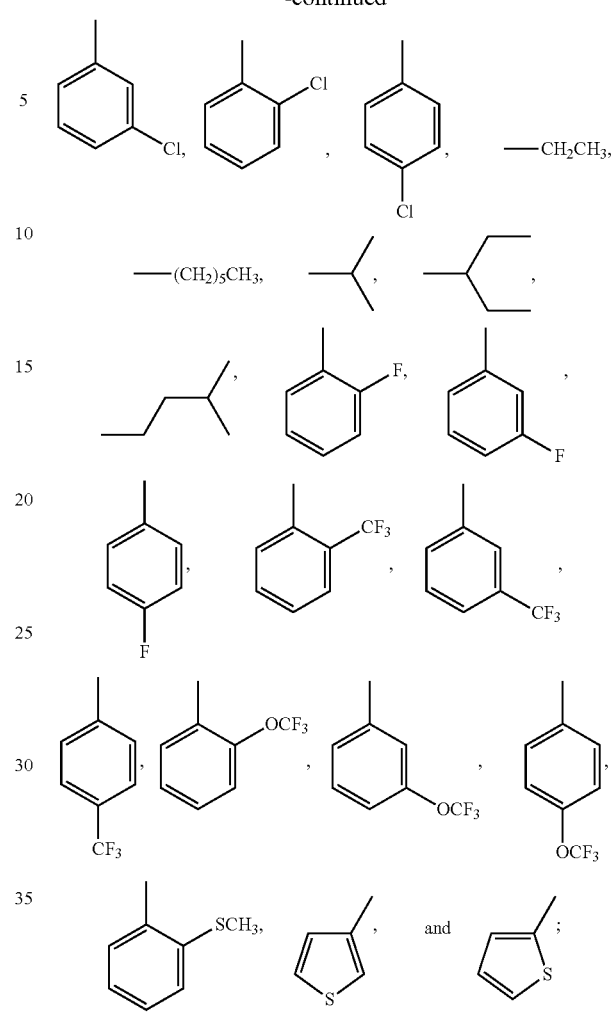
or a pharmaceutically acceptable salt thereof.
9. A compound of formula (Ic):
(Ic)
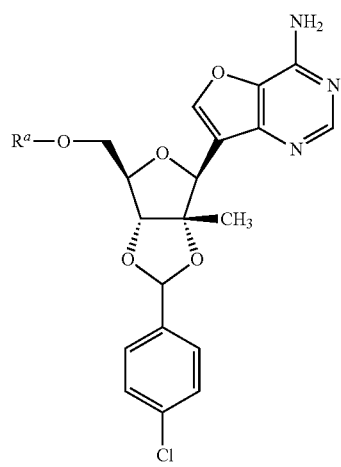

wherein $R^a$ is selected from
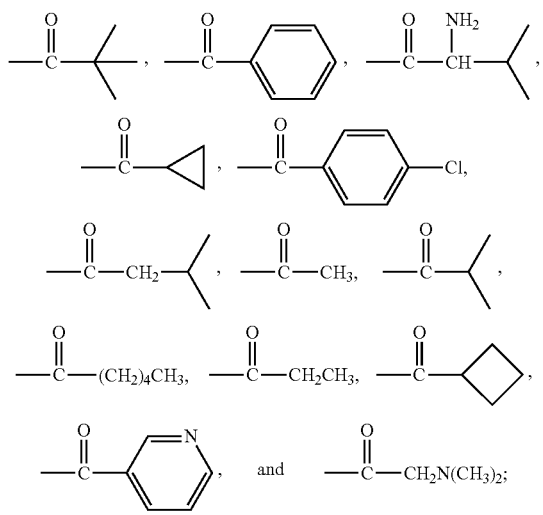
or a pharmaceutically acceptable salt thereof.
10. A compound of formula (Id):
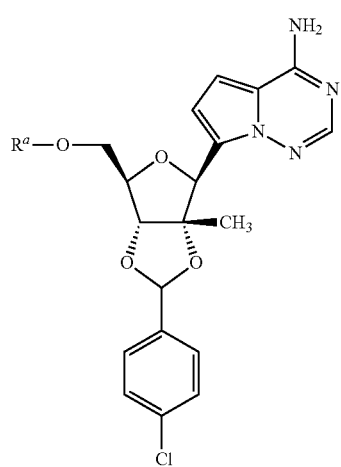
wherein $R^a$ is selected from
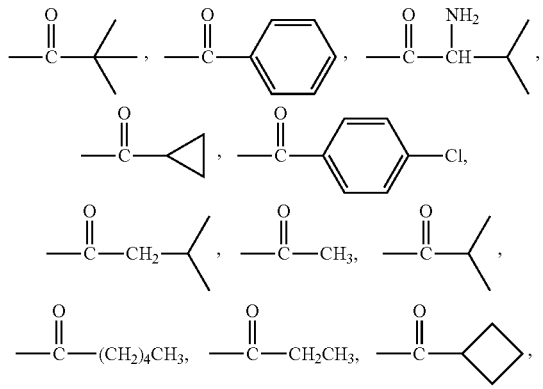
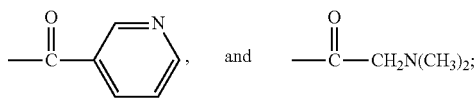
or a pharmaceutically acceptable salt thereof.
11. A compound of formula (Ie):
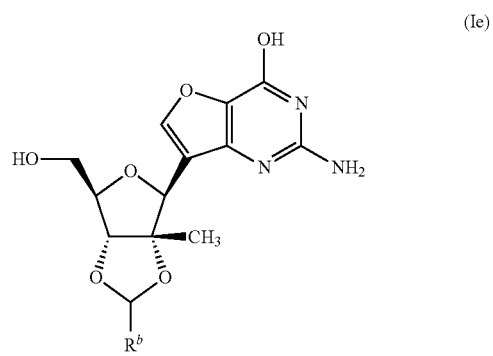
wherein $R^b$ is selected from:
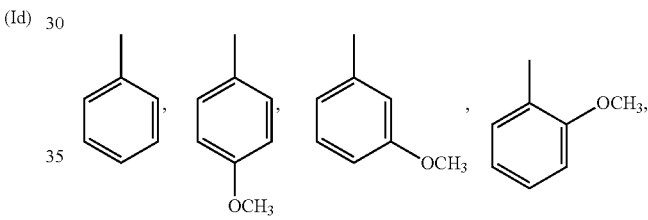
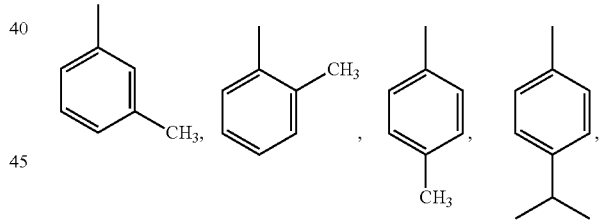
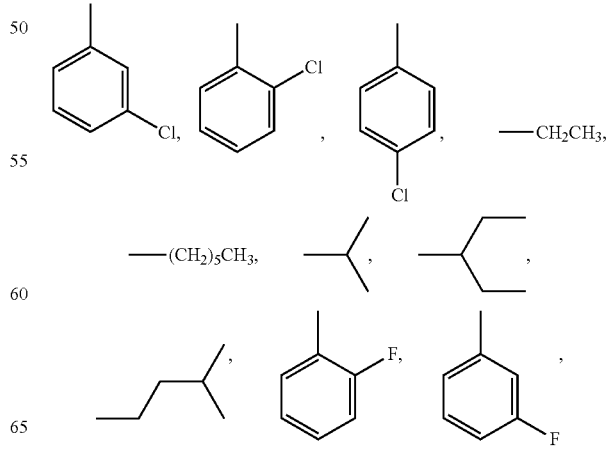

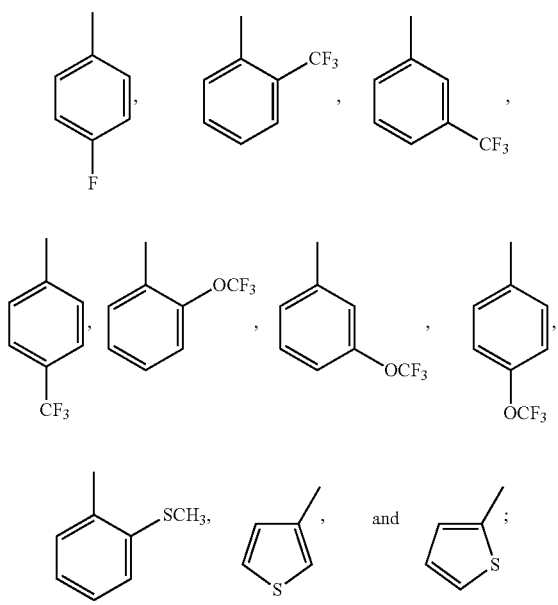
or a pharmaceutically acceptable salt thereof.
12. A compound of formula (If):
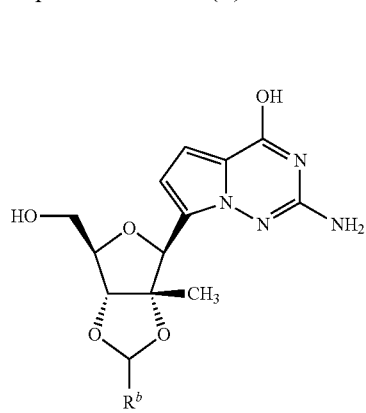
wherein $R^b$ is selected from:
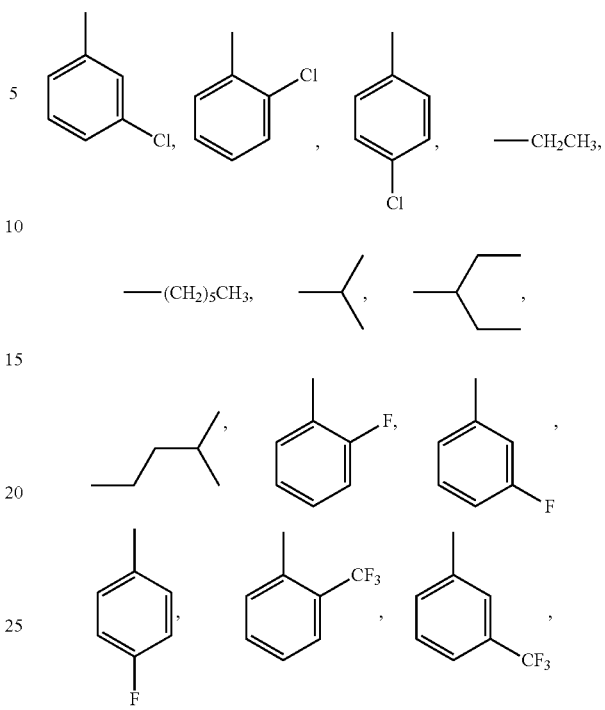
or a pharmaceutically acceptable salt thereof.
13. A compound of formula (Ig):

wherein $R^a$ is selected from

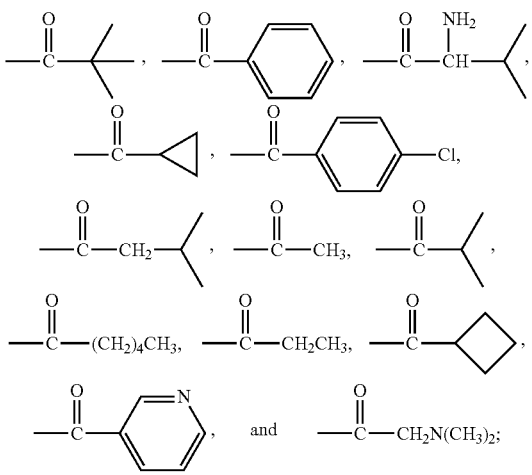

or a pharmaceutically acceptable salt thereof.

14. A compound of formula (Ih):

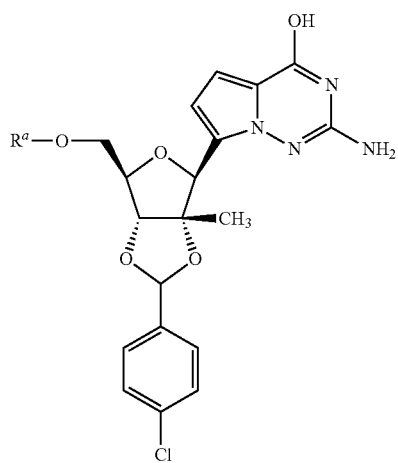

wherein $R^a$ is selected from

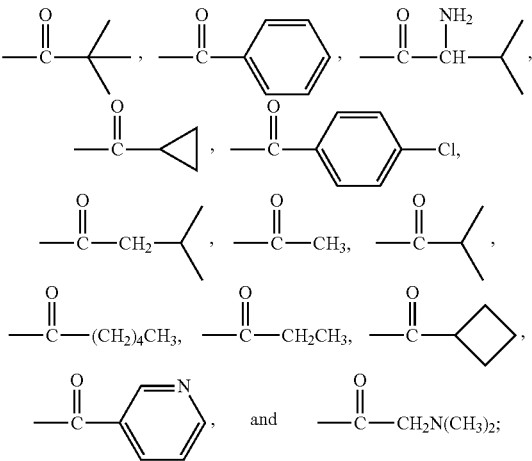

or a pharmaceutically acceptable salt thereof.

15. A pharmaceutical composition comprising a compound as described in claim 1 and a pharmaceutically acceptable carrier.

16. The composition of claim 15 which further comprises one or more additional anti-viral agents.

17. The composition of claim 16 wherein the one or more anti-viral agents are selected from ribavirin, levovirin, viramidine, thymosin alpha-1, an inhibitor of serine proteases, an inhibitor of inosine monophosphatedehydrognease, interferon-α, and pegylated interferon-α(peginterferon-α).

18. The composition of claim 15 which further comprises one or more additional HCV polymerase inhibitors.

19. The composition of claim 15 which further comprises one or more protease inhibitors.

20. The composition of claim 17 which further comprises ribavirin.

21. The composition of claim 17 which further comprises interferon-αor pegylated interferon-α(peginterferon-α).

22. The composition of claim 15 which further comprises one or more anti-cancer agents.

23. The composition of claim 22 wherein the one or more anti-cancer agents are selected from alkylating agents, antimetabolites, natural products, and hormonal agents.

24. A method for therapeutically treating a viral infection in an animal having a viral infection comprising administering to the animal a pharmaceutically effective amount of a compound as described in claim 1.

25. The method of claim 24 wherein the viral infection is selected from the group consisting of: hepatitis B, hepatitis C, human immunodeficiency virus, Polio, Coxsackie A and B, Rhino, Echo, small pox, Ebola, and West Nile virus.

26. The method of claim 24 wherein the viral infection is HCV.

27. The method of claim 24 which further comprises administering to the animal one or more additional HCV polymerase inhibitors.

28. The method of claim 24 which further comprises administering to the animal one or more protease inhibitors.

29. The method of claim 24 which further comprises administering ribavirin to the animal.

30. The method of claim 24 which further comprises administering interferon-αor pegylated interferon-α (peginterferon-α) to the animal.

31. A method for therapeutically treating cancer in an animal having cancer comprising administering to the animal a pharmaceutically effective amount of a compound as described in claim 1.

32. The method of claim 31 wherein one or more additional anti-cancer agents are administered.

33. The method of claim 24 wherein the animal is a human.

34. A method for inhibiting a viral RNA or DNA polymerase comprising contacting the polymerase in vitro or in vivo with an effective inhibitory amount of a compound as described in claim 1.

35. The method of claim 34 wherein the viral polymerase is an RdRp.

36. A pharmaceutical composition comprising a compound as described in claim 7 and a pharmaceutically acceptable carrier.

37. A pharmaceutical composition comprising a compound as described in claim 8 and a pharmaceutically acceptable carrier.

38. A pharmaceutical composition comprising a compound as described in claim 9 and a pharmaceutically acceptable carrier.

39. A pharmaceutical composition comprising a compound as described in claim 10 and a pharmaceutically acceptable carrier.

40. A pharmaceutical composition comprising a compound as described in claim 11 and a pharmaceutically acceptable carrier.

41. A pharmaceutical composition comprising a compound as described in claim 12 and a pharmaceutically acceptable carrier.

42. A pharmaceutical composition comprising a compound as described in claim 13 and a pharmaceutically acceptable carrier.

43. A pharmaceutical composition comprising a compound as described in claim 14 and a pharmaceutically acceptable carrier.

44. The method of claim 24, wherein the animal is a mammal.

45. The method of claim 31, wherein the animal is a mammal.

46. The method of claim 31, wherein the animal is a human.

* * * * *